(12) United States Patent
Zhou et al.

(10) Patent No.: US 12,325,749 B2
(45) Date of Patent: Jun. 10, 2025

(54) ANTI-PD-L1 ANTIBODY AND USE THEREOF

(71) Applicant: Beijing Sinotau Bio-Pharmaceuticals Technology Co., Ltd., Beijing (CN)

(72) Inventors: Tong Zhou, Birmingham, AL (US); Fengqi Cao, Beijing (CN); Zhe Li, Beijing (CN); Xiuli Jin, Beijing (CN)

(73) Assignee: Beijing Sinotau Bio-Pharmaceuticals Technology Co., Ltd., Beijing (CN)

( * ) Notice: Subject to any disclaimer, the term of this patent is extended or adjusted under 35 U.S.C. 154(b) by 753 days.

(21) Appl. No.: 17/628,536

(22) PCT Filed: Jul. 19, 2019

(86) PCT No.: PCT/CN2019/096786
§ 371 (c)(1),
(2) Date: Jan. 19, 2022

(87) PCT Pub. No.: WO2021/012092
PCT Pub. Date: Jan. 28, 2021

(65) Prior Publication Data
US 2022/0251211 A1 Aug. 11, 2022

(51) Int. Cl.
*C07K 16/28* (2006.01)
*A61K 39/395* (2006.01)

(52) U.S. Cl.
CPC ...... *C07K 16/2827* (2013.01); *A61K 39/3955* (2013.01); *C07K 2317/24* (2013.01); *C07K 2317/33* (2013.01); *C07K 2317/76* (2013.01); *C07K 2317/92* (2013.01)

(58) Field of Classification Search
CPC .. C07K 16/2809; C07K 16/18; C07K 16/246; C07K 16/2863; C07K 16/468; C07K 2317/31; C07K 2317/92; C07K 2317/94; C07K 2319/35; C07K 2319/50; C07K 2317/622; C07K 2318/10; C07K 16/2818; C07K 2318/00; C07K 16/46; A61K 2039/505
See application file for complete search history.

(56) References Cited

FOREIGN PATENT DOCUMENTS

| CN | 108112254 | 6/2018 |
|---|---|---|
| CN | 108112254 A | 6/2018 |
| WO | WO 2013/019906 A1 | 2/2013 |
| WO | WO 2013/019906 A9 | 2/2013 |
| WO | WO 2013/079174 A1 | 6/2013 |
| WO | WO 2016/149201 A2 | 9/2016 |
| WO | WO/2016/149201 | 9/2019 |

OTHER PUBLICATIONS

Yi et al. Biomarkers for predicting efficacy of PD-1/PD-L1 inhibitors. 2018. Molecular Cancer. 17:129; 2-14 (Year: 2018).*
Extended European Search Report from counterpart European Application No. 19938145.0 dated Jan. 12, 2023, 7 pages.
Written Opinion of the International Searching Authority in PCT/CN2019/096786, mailed Apr. 23, 2020 (4 pages).
International Search Report in PCT/CN2019/096786, mailed Apr. 23, 2020 (3 pages).
Corrected Version of Written Opinion of the International Searching Authority in PCT/CN2019/096786, mailed Mar. 11, 2021 (4 pages).
Corrected Version of International Search Report in PCT/CN2019/096786, mailed Mar. 11, 2021 (3 pages).

* cited by examiner

*Primary Examiner* — Misook Yu
*Assistant Examiner* — Grace H Lunde
(74) *Attorney, Agent, or Firm* — FINNEGAN, HENDERSON, FARABOW, GARRETT & DUNNER, LLP

(57) ABSTRACT

Provided is an isolated antibody or antigen-binding fragment thereof that binds specifically to human CD-L1 protein, a nucleic acid molecule encoding the same, therapeutic compositions thereof, and their use to treat a PD-L1 related disease, such as a tumor which is PD-L1 positive.

16 Claims, 17 Drawing Sheets
Specification includes a Sequence Listing.

Figure 1A. DNA sequence of the variable region of the m1F11 light chain
5'ATGGATTTTCAAGTGCAGATTTTCAGCTTCCTGCTAATCAGTGCCTCAGTCAT
GATATCCAGAGGACAAATTGTTCTCACCCAGTCTCCAGCAATCATGTCTGCATC
TCCAGGGGAGAAGGTCACCATGACCTGCAGTGCCAGCTCAAGTGTAAGTTCCA
TGCACTGGTACCAGCAGAAGTCAGGCACCTCCCCCAAAAGATGGATTTATGAC
ACATCCAAACTGGCTTCTGGAGTCCCTGCTCGCTTCAGTGGCAGTGGGTCTGG
GACCTCTTACTCTCTCACAATCAGCAGCATGGAGACTGAAGATGCTGCCACTTA
TTACTGCCAGCAGTGGAATAGTAACCCACCCACGTTCGGTGCTGGGACCAAGC
TGGAGCTGAAA3' (SEQ ID NO:1)

Figure 1B. Protein sequence of the variable region of the m1F11 light chain:
MDFQVQIFSFLLISASVMISRGQIVLTQSPAIMSASPGEKVTMTCSASSSVSSMHWY
QQKSGTSPKRWIYDTSKLASGVPARFSGSGSGTSYSLTISSMETEDAATYYCQQWN
SNPPTFGAGTKLELK (SEQ ID NO:2)

| Region | Sequence Fragment | Residues | Length |
|---|---|---|---|
| Leader | MDFQVQIFSFLLISASVMISRG (SEQ ID NO:3) | 1 - 22 | 22 |
| LFR1 | QIVLTQSPAIMSASPGEKVTMTC (SEQ ID NO:4) | 23 - 45 | 23 |
| CDR-L1 | SASSSVSSMH (SEQ ID NO:5) | 46 - 55 | 10 |
| LFR2 | WYQQKSGTSPKRWIY (SEQ ID NO:6) | 56 - 70 | 15 |
| CDR-L2 | DTSKLAS (SEQ ID NO:7) | 71 - 77 | 7 |
| LFR3 | GVPARFSGSGSGTSYSLTISSMETEDAATYYC (SEQ ID NO:8) | 78 - 109 | 32 |
| CDR-L3 | QQWNSNPPT (SEQ ID NO:9) | 110 - 118 | 9 |
| LFR4 | FGAGTKLELK (SEQ ID NO:10) | 119 - 128 | 10 |
| | | | 128 |

Figure 1C. DNA sequence of the variable region of the m1F11 heavy chain:
ATGGAATGGAACTGGGTCGTTCTCTTCCTCCTGTCATTAACTGCAGGTGTCTATG
CCCAGGGTCAGATGCAGCAGTCTGGAGCTGAACTGGTGAAGCCTGGGGCTTCA
GTGAAGCTGTCCTGCAAGACTTCTGGCTTCACCTTCAGCAGTAGCTATATAAGT
TGGTTGAAGCAAAAGTCTGGACAGAGTCTTGAGTGGATTGCATGGATTTATGCT
GGAACTGGTGGTACTGGCTATAATCAGAAGTTCACAGGCAAGGCCCAACTGAC
TGTAGACACATCCTCCAGCACAGCCTACATGCAATTCAGCAGCCTGACAACTG
AGGACTCTGCCATCTATTACTGTGCAATTTCCGCCTCCTATAGGTACGACGACCT
GTTTGCTTACTGGGGCCAAGGGACTCTGGTCACTGTCTCTGCA (SEQ ID NO:11)

Figure 1D. Protein sequence of the variable region of the m1F11 heavy chain:
MEWNWVVLFLLSLTAGVYAQGQMQQSGAELVKPGASVKLSCKTSGFTFSSSYIS
WLKQKSGQSLEWIAWIYAGTGGTGYNQKFTGKAQLTVDTSSSTAYMQFSSLTTED
SAIYYCAISASYRYDDLFAYWGQGTLVTVSA (SEQ ID NO:12)

| Region | Sequence Fragment | Residues | Length |
|---|---|---|---|
| Leader | MEWNWVVLFLLSLTAGVYA (SEQ ID NO:13) | 1 - 19 | 19 |
| HFR1 | QGQMQQSGAELVKPGASVKLSCKTSGFTFS (SEQ ID NO:14) | 20 - 49 | 30 |
| CDR-H1 | SSYIS (SEQ ID NO:15) | 50 - 54 | 5 |
| HFR2 | WLKQKSGQSLEWIA (SEQ ID NO:16) | 55 - 68 | 14 |
| CDR-H2 | WIYAGTGGTGYNQKFTG (SEQ ID NO:17) | 69 - 85 | 17 |
| HFR3 | KAQLTVDTSSSTAYMQFSSLTTEDSAIYYCAI (SEQ ID NO:18) | 86 - 117 | 32 |
| CDR-H3 | SASYRYDDLFAY (SEQ ID NO:19) | 118 - 129 | 12 |
| HFR4 | WGQGTLVTVSA (SEQ ID NO:20) | 130 - 140 | 11 |
| | | | 140 |

A

B

|  | Human PD-L1 | Cynomolgus PD-L1 | Mouse PD-L1 |
|---|---|---|---|
| $EC_{50}$(ng/ml) | 39.26 | 46.42 | NA |
| R square | 0.9932 | 0.9990 | NA |

Figure 6A. Protein sequence of the hu1F11 light chain
MDFQVQIFSFLLISASVMISRGQIVLTQSPASVSASPGEKVTITCSASSSVSSVHWYQ
QKSGTSPKRWIYDTSKLASGVPARFSGSGSGTSYSLTISSMETEDVATYYCQQWNS
NPPTFGTGTKLEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSP
VTKSFNRGEC (SEQ ID NO:21)

Figure 6B. Protein sequence of the hu1F11 heavy chain
MEWNWVVLFLLSLTAGVYAQVQLQQSGAELVKPGASVKLSCKTSGFTFSSSYISW
VKQSSGQGLEWIAWIYAGTGGTGYNQKFTGRASITVDTSTSTAYMQLSSLTSEDTA
IYYCAISASYRYDDLFAYWGQGTLVTVSSASTKGPSVFPLAPSSKSTSGGTAALGC
LVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYASTYRVVSVLTVLH
QDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQG
NVFSCSVMHEALHNHYTQKSLSLSPGK (SEQ ID NO:22)

Figure 6C. DNA sequence of the hu1F11 light chain
ATGGACTTCCAAGTTCAGATCTTCAGCTTTTTACTGATCAGCGCCAGCGTGATG
ATCAGCAGAGGCCAGATCGTGCTGACCCAGAGCCCCGCTAGCGTGAGCGCTAG
CCCCGGTGAGAAGGTGACCATCACTTGTTCCGCCAGCAGCAGCGTGAGCAGCG
TGCACTGGTACCAGCAGAAGAGCGGCACCAGCCCCAAGAGGTGGATCTACGA
CACCAGCAAGCTGGCCAGCGGAGTGCCCGCTAGATTTAGCGGCAGCGGCAGC
GGCACCAGCTACTCTTTAACCATCAGCAGCATGGAGACCGAGGACGTGGCCAC
CTACTACTGCCAGCAGTGGAACAGCAACCCCCCACCTTCGGCACTGGTACCA
AGCTGGAGATCAAGCGTACGGTGGCCGCCCCAGCGTGTTCATCTTTCCCCCCA
GCGACGAGCAGCTGAAGAGCGGCACAGCCAGCGTGGTGTGCCTGCTGAACAA
CTTCTACCCCAGGGAGGCCAAGGTGCAGTGGAAGGTGGACAACGCCCTGCAG
AGCGGCAACAGCCAGGAGAGCGTGACCGAGCAGGACAGCAAGGACAGCACC
TACAGCCTGAGCAGCACCCTGACCCTGAGCAAGGCCGACTACGAGAAGCACA
AGGTGTACGCCTGCGAGGTGACCCACCAGGGACTGAGCAGCCCCGTGACCAA
GAGCTTCAACAGGGGCGAGTGCTGA (SEQ ID NO:23)

Figure 6D. DNA sequence of the hu1F11 heavy chain:
ATGGAGTGGAACTGGGTGGTGCTGTTTTTACTGTCTTTAACCGCCGGCGTGTAC
GCTCAAGTTCAACTGCAGCAGAGCGGCGCCGAACTGGTGAAACCCGGTGCCA
GCGTGAAGCTGAGCTGCAAGACCTCCGGCTTCACCTTCAGCAGCAGCTACATC
AGCTGGGTGAAGCAGAGCAGCGGCCAAGGTTTAGAATGGATCGCTTGGATTTA
CGCCGGCACCGGCGGCACTGGTTATAACCAGAAGTTCACCGGTCGTGCCAGCA
TCACCGTCGACACCTCCACCAGCACCGCCTACATGCAGCTGAGCTCTTTAACCA
GCGAGGACACCGCCATCTACTACTGCGCCATCAGCGCCAGCTATCGTTACGACG
ATTTATTCGCCTACTGGGGACAAGGTACTTTAGTGACCGTGAGCAGCGCTAGCA
CCAAGGGCCCCAGCGTGTTTCCTCTGGCCCCTAGCTCCAAGTCCACCTCCGGA
GGAACAGCCGCCCTGGGATGCCTCGTGAAGGACTACTTCCCTGAGCCCGTGAC
CGTGTCCTGGAACAGCGGAGCCCTGACAAGCGGAGTGCACACCTTCCCCGCC
GTGCTGCAGTCCAGCGGACTGTACAGCCTGAGCAGCGTGGTGACCGTGCCTTC
CTCCAGCCTCGGCACCCAGACCTACATCTGCAACGTGAACCACAAGCCCTCCA
ACACAAAGGTCGACAAGAAGGTGGAGCCCAAGAGCTGCGACAAGACCCACA
CCTGCCCTCCCTGCCCTGCTCCTGAACTCCTGGGAGGCCCCAGCGTCTTCCTGT
TTCCCCCCAAACCCAAGGACACACTGATGATCAGCAGAACCCCTGAGGTGACC
TGCGTGGTGGTCGATGTGTCCCACGAGGACCCCGAGGTGAAGTTCAATTGGTA
CGTGGACGGCGTCGAGGTGCACAACGCCAAAACAAAGCCCAGAGAAGAGCA
GTACGCCTCCACCTACAGAGTCGTGTCCGTGCTGACAGTGCTGCACCAGGACT
GGCTGAACGGCAAGGAGTACAAGTGCAAGGTGAGCAACAAGGCCCTGCCTGC
CCCCATCGAGAAGACCATCAGCAAGGCCAAAGGCCAGCCCAGAGAGCCTCAG
GTGTACACCCTGCCCCCAGCAGGGAAGAGATGACCAAGAATCAGGTGAGCCT
GACCTGCCTGGTGAAAGGCTTCTATCCCAGCGACATCGCCGTGGAGTGGGAGA
GCAACGGCCAGCCCGAGAACAACTACAAGACCACCCCTCCCGTGCTGGACAG
CGATGGCTCCTTCTTCCTGTACAGCAAGCTGACCGTGGACAAGAGCAGGTGGC
AGCAGGGCAACGTCTTCAGCTGCAGCGTGATGCATGAGGCCCTGCACAACCAT
TACACCCAGAAGTCCCTGAGCCTGTCCCTGGCAAGTGA (SEQ ID NO:24)

Figure 6E. Protein sequence of the variable region of the hu1F11 light chain
QIVLTQSPASVSASPGEKVTITCSASSSVSSVHWYQQKSGTSPKRWIYDTSKLASG
VPARFSGSGSGTSYSLTISSMETEDVATYYCQQWNSNPPTFGTGTKLEIK (SEQ ID
NO:25)

Figure 6F. Protein sequence of the constant region of the hu1F11 light chain
RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC (SEQ
ID NO:26)

Figure 6G. Protein sequence of the variable region of the hu1F11 heavy chain
QVQLQQSGAELVKPGASVKLSCKTSGFTFSSSYISWVKQSSGQGLEWIAWIYAGT
GGTGYNQKFTGRASITVDTSTSTAYMQLSSLTSEDTAIYYCAISASYRYDDLFAYW
GQGTLVTVSS (SEQ ID NO:27)

Figure 6H. Protein sequence of the constant region of the hu1F11 heavy chain
ASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEV
HNAKTKPREEQYASTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPGK
(SEQ ID NO:28)

Figure 6I. DNA sequence of the variable region of the hu1F11 light chain
CAGATCGTGCTGACCCAGAGCCCCGCTAGCGTGAGCGCTAGCCCCGGTGAGAA
GGTGACCATCACTTGTTCCGCCAGCAGCAGCGTGAGCAGCGTGCACTGGTACC
AGCAGAAGAGCGGCACCAGCCCCAAGAGGTGGATCTACGACACCAGCAAGCT
GGCCAGCGGAGTGCCCGCTAGATTTAGCGGCAGCGGCAGCGGCACCAGCTACT
CTTTAACCATCAGCAGCATGGAGACCGAGGACGTGGCCACCTACTACTGCCAG
CAGTGGAACAGCAACCCCCCCACCTTCGGCACTGGTACCAAGCTGGAGATCAA
G (SEQ ID NO:29)

Figure 6J. DNA sequence of the constant region of the hu1F11 light chain
CGTACGGTGGCCGCCCCCAGCGTGTTCATCTTTCCCCCCAGCGACGAGCAGCT
GAAGAGCGGCACAGCCAGCGTGGTGTGCCTGCTGAACAACTTCTACCCCAGG
GAGGCCAAGGTGCAGTGGAAGGTGGACAACGCCCTGCAGAGCGGCAACAGCC
AGGAGAGCGTGACCGAGCAGGACAGCAAGGACAGCACCTACAGCCTGAGCAG
CACCCTGACCCTGAGCAAGGCCGACTACGAGAAGCACAAGGTGTACGCCTGC
GAGGTGACCCACCAGGGACTGAGCAGCCCCGTGACCAAGAGCTTCAACAGGG
GCGAGTGC (SEQ ID NO:30)

Figure 6K. DNA sequence of the constant region of the hu1F11 heavy chain
CAAGTTCAACTGCAGCAGAGCGGCGCCGAACTGGTGAAACCCGGTGCCAGCG
TGAAGCTGAGCTGCAAGACCTCCGGCTTCACCTTCAGCAGCAGCTACATCAGC
TGGGTGAAGCAGAGCAGCGGCCAAGGTTTAGAATGGATCGCTTGGATTTACGC
CGGCACCGGCGGCACTGGTTATAACCAGAAGTTCACCGGTCGTGCCAGCATCA
CCGTCGACACCTCCACCAGCACCGCCTACATGCAGCTGAGCTCTTTAACCAGC
GAGGACACCGCCATCTACTACTGCGCCATCAGCGCCAGCTATCGTTACGACGAT
TTATTCGCCTACTGGGGACAAGGTACTTTAGTGACCGTGAGCAGC (SEQ ID
NO:31)

Figure 6L. DNA sequence of the constant region of the hu1F11 heavy chain
GCTAGCACCAAGGGCCCCAGCGTGTTTCCTCTGGCCCCTAGCTCCAAGTCCAC
CTCCGGAGGAACAGCCGCCCTGGGATGCCTCGTGAAGGACTACTTCCCTGAGC
CCGTGACCGTGTCCTGGAACAGCGGAGCCCTGACAAGCGGAGTGCACACCTT
CCCCGCCGTGCTGCAGTCCAGCGGACTGTACAGCCTGAGCAGCGTGGTGACCG
TGCCTTCCTCCAGCCTCGGCACCCAGACCTACATCTGCAACGTGAACCACAAG
CCCTCCAACACAAAGGTCGACAAGAAGGTGGAGCCCAAGAGCTGCGACAAGA
CCCACACCTGCCCTCCCTGCCCTGCTCCTGAACTCCTGGGAGGCCCCAGCGTC
TTCCTGTTTCCCCCCAAACCCAAGGACACACTGATGATCAGCAGAACCCCTGA
GGTGACCTGCGTGGTGGTCGATGTGTCCACGAGGACCCCGAGGTGAAGTTCA
ATTGGTACGTGGACGGCGTCGAGGTGCACAACGCCAAAACAAAGCCCAGAGA
AGAGCAGTACGCCTCCACCTACAGAGTCGTGTCCGTGCTGACAGTGCTGCACC
AGGACTGGCTGAACGGCAAGGAGTACAAGTGCAAGGTGAGCAACAAGGCCCT
GCCTGCCCCCATCGAGAAGACCATCAGCAAGGCCAAAGGCCAGCCCAGAGAG
CCTCAGGTGTACACCCTGCCCCCAGCAGGGAAGAGATGACCAAGAATCAGGT
GAGCCTGACCTGCCTGGTGAAAGGCTTCTATCCCAGCGACATCGCCGTGGAGT
GGGAGAGCAACGGCCAGCCCGAGAACAACTACAAGACCACCCCTCCCGTGCT
GGACAGCGATGGCTCCTTCTTCCTGTACAGCAAGCTGACCGTGGACAAGAGCA
GGTGGCAGCAGGGCAACGTCTTCAGCTGCAGCGTGATGCATGAGGCCCTGCAC
AACCATTACACCCAGAAGTCCCTGAGCCTGTCCCCTGGCAAG (SEQ ID NO:32)

A.

B.

| ka(1/Ms) | kd(1/s) | KD(M) | Rmax(RU) | Chi$^2$(RU$^2$) | Model |
|---|---|---|---|---|---|
| 2.09×10$^5$ | 5.76×10$^{-4}$ | 2.75×10$^{-9}$ | 16.3 | 0.14 | 1:1binding |

A.

B.

|  | Atezolizumab | Avelumab | chimeric 1F11 | humanized 1F11 |
|---|---|---|---|---|
| $EC_{50}$ (ng/ml) | 54.45 | 120.9 | 81.01 | 74.24 |
| R square | 0.9966 | 0.9904 | 0.9964 | 0.9928 |

A
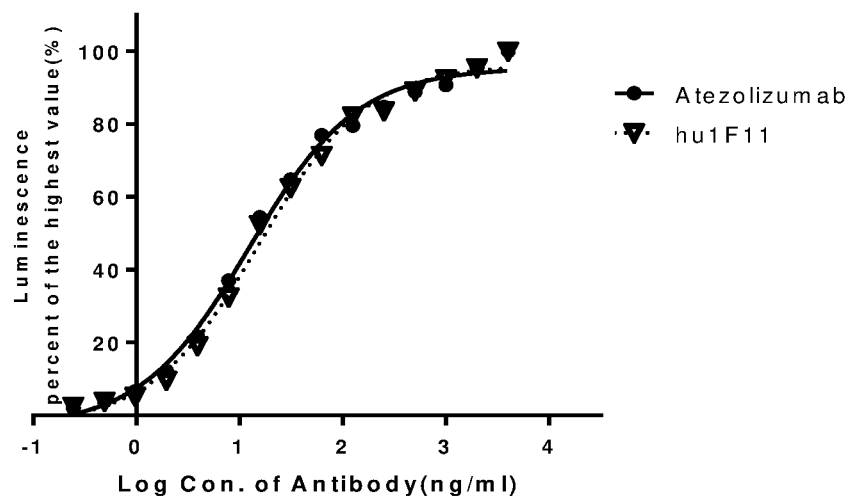
B
|  | hu1F11 | Atezolizumab |
|---|---|---|
| $EC_{50}$ (ng/ml) | 15.26 | 12.36 |
| R square | 0.9952 | 0.9951 |
C
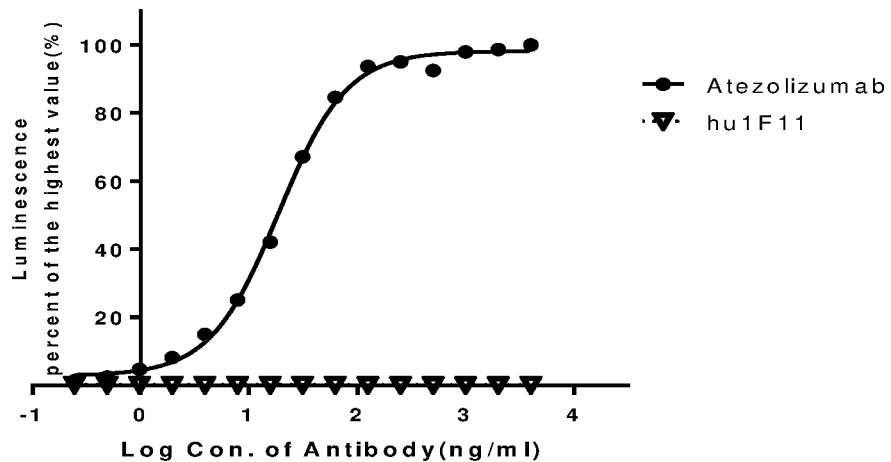
D
|  | hu1F11 | Atezolizumab |
|---|---|---|
| $EC_{50}$ (ng/ml) | NA | 18.66 |
| R square | NA | 0.9979 |
Figure 10

SEQUENCE LISTING

```
<160> NUMBER OF SEQ ID NOS: 33

<210> SEQ ID NO 1
<211> LENGTH: 384
<212> TYPE: DNA
<213> ORGANISM: Artificial Sequence
<220> FEATURE:
<223> OTHER INFORMATION: DNA sequence of the variable region of the
      m1F11 light chain

<400> SEQUENCE: 1
atggattttc aagtgcagat tttcagcttc ctgctaatca gtgcctcagt catgatatcc      60
agaggacaaa ttgttctcac ccagtctcca gcaatcatgt ctgcatctcc aggggagaag     120
gtcaccatga cctgcagtgc cagctcaagt gtaagttcca tgcactggta ccagcagaag     180
tcaggcacct cccccaaaag atggatttat gacacatcca aactggcttc tggagtccct     240
```

```
gctcgcttca gtggcagtgg gtctgggacc tcttactctc tcacaatcag cagcatggag    300
actgaagatg ctgccactta ttactgccag cagtggaata gtaacccacc cacgttcggt    360
gctgggacca agctggagct gaaa                                           384
```

<210> SEQ ID NO 2
<211> LENGTH: 128
<212> TYPE: PRT
<213> ORGANISM: Artificial Sequence
<220> FEATURE:
<223> OTHER INFORMATION: Protein sequence of the variable region of the
      m1F11 light chain

<400> SEQUENCE: 2

```
Met Asp Phe Gln Val Gln Ile Phe Ser Phe Leu Leu Ile Ser Ala Ser
1               5                   10                  15

Val Met Ile Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Ser Met His Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Thr Glu Asp Ala Ala Thr Tyr Tyr Cys Gln Gln Trp
            100                 105                 110

Asn Ser Asn Pro Pro Thr Phe Gly Ala Gly Thr Lys Leu Glu Leu Lys
        115                 120                 125
```

<210> SEQ ID NO 3
<211> LENGTH: 22
<212> TYPE: PRT
<213> ORGANISM: Artificial Sequence
<220> FEATURE:
<223> OTHER INFORMATION: Leader of the variable region of the m1F11
      light chain

<400> SEQUENCE: 3

```
Met Asp Phe Gln Val Gln Ile Phe Ser Phe Leu Leu Ile Ser Ala Ser
1               5                   10                  15

Val Met Ile Ser Arg Gly
            20
```

<210> SEQ ID NO 4
<211> LENGTH: 23
<212> TYPE: PRT
<213> ORGANISM: Artificial Sequence
<220> FEATURE:
<223> OTHER INFORMATION: LFR1 of of the variable region of the m1F11
      light chain

<400> SEQUENCE: 4

```
Gln Ile Val Leu Thr Gln Ser Pro Ala Ile Met Ser Ala Ser Pro Gly
1               5                   10                  15

Glu Lys Val Thr Met Thr Cys
            20
```

<210> SEQ ID NO 5
<211> LENGTH: 10

```
<212> TYPE: PRT
<213> ORGANISM: Artificial Sequence
<220> FEATURE:
<223> OTHER INFORMATION: CDR-L1 of the variable region of the m1F11
      light chain

<400> SEQUENCE: 5

Ser Ala Ser Ser Ser Val Ser Ser Met His
1               5                   10

<210> SEQ ID NO 6
<211> LENGTH: 15
<212> TYPE: PRT
<213> ORGANISM: Artificial Sequence
<220> FEATURE:
<223> OTHER INFORMATION: LFR2 of the variable region of the m1F11 light
      chain

<400> SEQUENCE: 6

Trp Tyr Gln Gln Lys Ser Gly Thr Ser Pro Lys Arg Trp Ile Tyr
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: CDR-L2 of the variable region of the m1F11
      light chain

<400> SEQUENCE: 7

Asp Thr Ser Lys Leu Ala Ser
1               5

<210> SEQ ID NO 8
<211> LENGTH: 32
<212> TYPE: PRT
<213> ORGANISM: Artificial Sequence
<220> FEATURE:
<223> OTHER INFORMATION: LFR3 of the variable region of the m1F11 light
      chain

<400> SEQUENCE: 8

Gly Val Pro Ala Arg Phe Ser Gly Ser Gly Ser Gly Thr Ser Tyr Ser
1               5                   10                  15

Leu Thr Ile Ser Ser Met Glu Thr Glu Asp Ala Ala Thr Tyr Tyr Cys
            20                  25                  30

<210> SEQ ID NO 9
<211> LENGTH: 9
<212> TYPE: PRT
<213> ORGANISM: Artificial Sequence
<220> FEATURE:
<223> OTHER INFORMATION: CDR-L3 of the variable region of the m1F11
      light chain

<400> SEQUENCE: 9

Gln Gln Trp Asn Ser Asn Pro Pro Thr
1               5

<210> SEQ ID NO 10
<211> LENGTH: 10
<212> TYPE: PRT
<213> ORGANISM: Artificial Sequence
<220> FEATURE:
<223> OTHER INFORMATION: LFR4 of the variable region of the m1F11 light
      chain
```

<400> SEQUENCE: 10

Phe Gly Ala Gly Thr Lys Leu Glu Leu Lys
1               5                   10

<210> SEQ ID NO 11
<211> LENGTH: 420
<212> TYPE: DNA
<213> ORGANISM: Artificial Sequence
<220> FEATURE:
<223> OTHER INFORMATION: DNA sequence of the variable region of the
      m1F11 heavy chain

<400> SEQUENCE: 11

```
atggaatgga actgggtcgt tctcttcctc ctgtcattaa ctgcaggtgt ctatgcccag    60
ggtcagatgc agcagtctgg agctgaactg gtgaagcctg gggcttcagt gaagctgtcc   120
tgcaagactt ctggcttcac cttcagcagt agctatataa gttggttgaa gcaaaagtct   180
ggacagagtc ttgagtggat tgcatggatt tatgctggaa ctggtggtac tggctataat   240
cagaagttca caggcaaggc caactgact gtagacacat cctccagcac agcctacatg    300
caattcagca gcctgacaac tgaggactct gccatctatt actgtgcaat tccgcctcc   360 tataggtacg acgacctgtt tgcttactgg ggccaaggga ctctggtcac tgtctctgca   420
```

<210> SEQ ID NO 12
<211> LENGTH: 140
<212> TYPE: PRT
<213> ORGANISM: Artificial Sequence
<220> FEATURE:
<223> OTHER INFORMATION: Protein sequence of the variable region of the
      m1F11 heavy chain

<400> SEQUENCE: 12

Met Glu Trp Asn Trp Val Val Leu Phe Leu Leu Ser Leu Thr Ala Gly
1               5                   10                  15

Val Tyr Ala Gln Gly Gln Met Gln Gln Ser Gly Ala Glu Leu Val Lys
            20                  25                  30

Pro Gly Ala Ser Val Lys Leu Ser Cys Lys Thr Ser Gly Phe Thr Phe
        35                  40                  45

Ser Ser Ser Tyr Ile Ser Trp Leu Lys Gln Lys Ser Gly Gln Ser Leu
    50                  55                  60

Glu Trp Ile Ala Trp Ile Tyr Ala Gly Thr Gly Gly Thr Gly Tyr Asn
65                  70                  75                  80

Gln Lys Phe Thr Gly Lys Ala Gln Leu Thr Val Asp Thr Ser Ser Ser
                85                  90                  95

Thr Ala Tyr Met Gln Phe Ser Ser Leu Thr Thr Glu Asp Ser Ala Ile
            100                 105                 110

Tyr Tyr Cys Ala Ile Ser Ala Ser Tyr Arg Tyr Asp Asp Leu Phe Ala
        115                 120                 125

Tyr Trp Gly Gln Gly Thr Leu Val Thr Val Ser Ala
    130                 135                 140

<210> SEQ ID NO 13
<211> LENGTH: 19
<212> TYPE: PRT
<213> ORGANISM: Artificial Sequence
<220> FEATURE:
<223> OTHER INFORMATION: Leader of the variable region of the m1F11
      heavy chain

<400> SEQUENCE: 13

Met Glu Trp Asn Trp Val Val Leu Phe Leu Leu Ser Leu Thr Ala Gly
1               5                   10                  15

Val Tyr Ala

<210> SEQ ID NO 14
<211> LENGTH: 30
<212> TYPE: PRT
<213> ORGANISM: Artificial Sequence
<220> FEATURE:
<223> OTHER INFORMATION: HFR1 of the variable region of the m1F11 heavy
      chain

<400> SEQUENCE: 14

Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser
            20                  25                  30

<210> SEQ ID NO 15
<211> LENGTH: 5
<212> TYPE: PRT
<213> ORGANISM: Artificial Sequence
<220> FEATURE:
<223> OTHER INFORMATION: CDR-H1 of the variable region of the m1F11
      heavy chain

<400> SEQUENCE: 15

Ser Ser Tyr Ile Ser
1               5

<210> SEQ ID NO 16
<211> LENGTH: 14
<212> TYPE: PRT
<213> ORGANISM: Artificial Sequence
<220> FEATURE:
<223> OTHER INFORMATION: HFR2 of the variable region of the m1F11 heavy
      chain

<400> SEQUENCE: 16

Trp Leu Lys Gln Lys Ser Gly Gln Ser Leu Glu Trp Ile Ala
1               5                   10

<210> SEQ ID NO 17
<211> LENGTH: 17
<212> TYPE: PRT
<213> ORGANISM: Artificial Sequence
<220> FEATURE:
<223> OTHER INFORMATION: CDR-H2 of the variable region of the m1F11
      heavy chain

<400> SEQUENCE: 17

Trp Ile Tyr Ala Gly Thr Gly Gly Thr Gly Tyr Asn Gln Lys Phe Thr
1               5                   10                  15

Gly

<210> SEQ ID NO 18
<211> LENGTH: 32
<212> TYPE: PRT
<213> ORGANISM: Artificial Sequence
<220> FEATURE:
<223> OTHER INFORMATION: HFR3 of the variable region of the m1F11 heavy
      chain

<400> SEQUENCE: 18

Lys Ala Gln Leu Thr Val Asp Thr Ser Ser Ser Thr Ala Tyr Met Gln
1               5                   10                  15

```
Phe Ser Ser Leu Thr Thr Glu Asp Ser Ala Ile Tyr Tyr Cys Ala Ile
            20                  25                  30

<210> SEQ ID NO 19
<211> LENGTH: 12
<212> TYPE: PRT
<213> ORGANISM: Artificial Sequence
<220> FEATURE:
<223> OTHER INFORMATION: CDR-H3 of the variable region of the m1F11
      heavy chain

<400> SEQUENCE: 19

Ser Ala Ser Tyr Arg Tyr Asp Asp Leu Phe Ala Tyr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: HFR4 of the variable region of the m1F11 heavy
      chain

<400> SEQUENCE: 20

Trp Gly Gln Gly Thr Leu Val Thr Val Ser
1               5                   10

<210> SEQ ID NO 21
<211> LENGTH: 235
<212> TYPE: PRT
<213> ORGANISM: Artificial Sequence
<220> FEATURE:
<223> OTHER INFORMATION: Protein sequence of the hu1F11 light chain

<400> SEQUENCE: 21

Met Asp Phe Gln Val Gln Ile Phe Ser Phe Leu Leu Ile Ser Ala Ser
1               5                   10                  15

Val Met Ile Ser Arg Gly Gln Ile Val Leu Thr Gln Ser Pro Ala Ser
            20                  25                  30

Val Ser Ala Ser Pro Gly Glu Lys Val Thr Ile Thr Cys Ser Ala Ser
        35                  40                  45

Ser Ser Val Ser Ser Val His Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Thr Glu Asp Val Ala Thr Tyr Tyr Cys Gln Gln Trp
            100                 105                 110

Asn Ser Asn Pro Pro Thr Phe Gly Thr Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
```

```
                195                 200                 205
Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 22
<211> LENGTH: 470
<212> TYPE: PRT
<213> ORGANISM: Artificial Sequence
<220> FEATURE:
<223> OTHER INFORMATION: Protein sequence of the hu1F11 heavy chain

<400> SEQUENCE: 22

Met Glu Trp Asn Trp Val Val Leu Phe Leu Leu Ser Leu Thr Ala Gly
1               5                   10                  15

Val Tyr Ala Gln Val Gln Leu Gln Gln Ser Gly Ala Glu Leu Val Lys
            20                  25                  30

Pro Gly Ala Ser Val Lys Leu Ser Cys Lys Thr Ser Gly Phe Thr Phe
        35                  40                  45

Ser Ser Ser Tyr Ile Ser Trp Val Lys Gln Ser Ser Gly Gln Gly Leu
    50                  55                  60

Glu Trp Ile Ala Trp Ile Tyr Ala Gly Thr Gly Gly Thr Gly Tyr Asn
65                  70                  75                  80

Gln Lys Phe Thr Gly Arg Ala Ser Ile Thr Val Asp Thr Ser Thr Ser
                85                  90                  95

Thr Ala Tyr Met Gln Leu Ser Ser Leu Thr Ser Glu Asp Thr Ala Ile
            100                 105                 110

Tyr Tyr Cys Ala Ile Ser Ala Ser Tyr Arg Tyr Asp Asp Leu Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Ala
305                 310                 315                 320

Ser Thr Tyr Arg Val Val Ser Val Leu Thr Val Leu His Gln Asp Trp
```

```
                    325                 330                 335
Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 23
<211> LENGTH: 708
<212> TYPE: DNA
<213> ORGANISM: Artificial Sequence
<220> FEATURE:
<223> OTHER INFORMATION: DNA sequence of the hu1F11 light chain

<400> SEQUENCE: 23
atggacttcc aagttcagat cttcagcttt ttactgatca gcgccagcgt gatgatcagc      60
agaggccaga tcgtgctgac ccagagcccc gctagcgtga gcgctagccc cggtgagaag     120
gtgaccatca cttgttccgc cagcagcagc gtgagcagcg tgcactggta ccagcagaag     180
agcggcacca gccccaagag gtggatctac gacaccagca gctggccag cggagtgccc      240 gctagattta gcggcagcgg cagcggcacc agctactctt taaccatcag cagcatggag     300
accgaggacg tggccaccta ctactgccag cagtggaaca gcaaccccc caccttcggc      360 actggtacca gctggagat caagcgtacg gtggccgccc ccagcgtgtt catctttccc      420
cccagcgacg agcagctgaa gagcggcaca gccagcgtgg tgtgcctgct gaacaacttc     480
taccccaggg aggccaaggt gcagtggaag gtggacaacg ccctgcagag cggcaacagc     540
caggagagcg tgaccgagca ggacagcaag gacagcacct acagcctgag cagcaccctg     600
accctgagca aggccgacta cgagaagcac aaggtgtacg cctgcgaggt gacccaccag     660
ggactgagca gccccgtgac caagagcttc aacaggggcg agtgctga                  708

<210> SEQ ID NO 24
<211> LENGTH: 1413
<212> TYPE: DNA
<213> ORGANISM: Artificial Sequence
<220> FEATURE:
<223> OTHER INFORMATION: DNA sequence of the hu1F11 heavy chain

<400> SEQUENCE: 24
atggagtgga actgggtggt gctgttttta ctgtctttaa ccgccggcgt gtacgctcaa      60
gttcaactgc agcagagcgg cgccgaactg gtgaaaccg gtgccagcgt gaagctgagc      120
tgcaagacct ccggcttcac cttcagcagc agctacatca gctgggtgaa gcagagcagc     180
```

```
ggccaaggtt tagaatggat cgcttggatt tacgccggca ccggcggcac tggttataac      240
cagaagttca ccggtcgtgc cagcatcacc gtcgacacct ccaccagcac cgcctacatg      300
cagctgagct ctttaaccag cgaggacacc gccatctact actgcgccat cagcgccagc      360
tatcgttacg acgatttatt cgcctactgg ggacaaggta cttttagtga cgtgagcagc      420
gctagcacca agggccccag cgtgtttcct ctggccccta gctccaagtc cacctccgga      480
ggaacagccg ccctgggatg cctcgtgaag gactacttcc ctgagcccgt gaccgtgtcc      540
tggaacagcg gagccctgac aagcggagtg cacaccttcc cgccgtgct gcagtccagc      600 ggactgtaca gcctgagcag cgtggtgacc gtgccttcct ccagcctcgg cacccagacc      660
tacatctgca acgtgaacca caagccctcc aacacaaagg tcgacaagaa ggtggagccc      720
aagagctgcg acaagaccca cacctgcccc cctgccctg ctcctgaact cctgggaggc      780
cccagcgtct tcctgttttcc ccccaaaccc aaggacacac tgatgatcag cagaaccccct      840 gaggtgaccct gcgtggtggt cgatgtgtcc cacgaggacc ccgaggtgaa gttcaattgg      900
tacgtggacg gcgtcgaggt gcacaacgcc aaaacaaagc cagagaaga gcagtacgcc      960 tccacctaca gagtcgtgtc cgtgctgaca gtgctgcacc aggactggct gaacggcaag     1020
gagtacaagt gcaaggtgag caacaaggcc ctgcctgccc catcgagaa gaccatcagc     1080 aaggccaaag gccagcccag agagcctcag gtgtacaccc tgcccccag cagggaagag     1140 atgaccaaga atcaggtgag cctgacctgc ctggtgaaag gcttctatcc agcgacatc     1200 gccgtggagt gggagagcaa cggccagccc gagaacaact acaagaccac ccctcccgtg     1260
ctggacagcg atggctcctt cttcctgtac agcaagctga ccgtggacaa gagcaggtgg     1320
cagcagggca acgtcttcag ctgcagcgtg atgcatgagg ccctgcacaa ccattacacc     1380
cagaagtccc tgagcctgtc ccctggcaag tga                                  1413
```

<210> SEQ ID NO 25
<211> LENGTH: 106
<212> TYPE: PRT
<213> ORGANISM: Artificial Sequence
<220> FEATURE:
<223> OTHER INFORMATION: Protein sequence of the variable region of the
      hu1F11 light chain

<400> SEQUENCE: 25

Gln Ile Val Leu Thr Gln Ser Pro Ala Ser Val Ser Ala Ser Pro Gly
1               5                   10                  15

Glu Lys Val Thr Ile Thr Cys Ser Ala Ser Ser Val Ser Ser Val
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Thr Glu
65                  70                  75                  80

Asp Val Ala Thr Tyr Tyr Cys Gln Gln Trp Asn Ser Asn Pro Pro Thr
                85                  90                  95

Phe Gly Thr Gly Thr Lys Leu Glu Ile Lys
            100                 105

<210> SEQ ID NO 26
<211> LENGTH: 107
<212> TYPE: PRT
<213> ORGANISM: Artificial Sequence

```
<220> FEATURE:
<223> OTHER INFORMATION: Protein sequence of the constant region of the
      hu1F11 light chain

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 121
<212> TYPE: PRT
<213> ORGANISM: Artificial Sequence
<220> FEATURE:
<223> OTHER INFORMATION: Protein sequence of the variable region of the
      hu1F11 heavy chain

<400> SEQUENCE: 27

Gln Val Gln Leu Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Ser
            20                  25                  30

Tyr Ile Ser Trp Val Lys Gln Ser Ser Gly Gln Gly Leu Glu Trp Ile
        35                  40                  45

Ala Trp Ile Tyr Ala Gly Thr Gly Gly Thr Gly Tyr Asn Gln Lys Phe
    50                  55                  60

Thr Gly Arg Ala Ser Ile Thr Val Asp Thr Ser Ser Thr Ala Tyr
65                  70                  75                  80

Met Gln Leu Ser Ser Leu Thr Ser Glu Asp Thr Ala Ile Tyr Tyr Cys
                85                  90                  95

Ala Ile Ser Ala Ser Tyr Arg Tyr Asp Asp Leu Phe Ala Tyr Trp Gly
            100                 105                 110

Gln Gly Thr Leu Val Thr Val Ser Ser
        115                 120

<210> SEQ ID NO 28
<211> LENGTH: 330
<212> TYPE: PRT
<213> ORGANISM: Artificial Sequence
<220> FEATURE:
<223> OTHER INFORMATION: Protein sequence of the constant region of the
      hu1F11 heavy chain

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 318
<212> TYPE: DNA
<213> ORGANISM: Artificial Sequence
<220> FEATURE:
<223> OTHER INFORMATION: DNA sequence of the variable region of the
      hu1F11 light chain

<400> SEQUENCE: 29
cagatcgtgc tgacccagag ccccgctagc gtgagcgcta gccccggtga aggtgacc        60 atcacttgtt ccgccagcag cagcgtgagc agcgtgcact ggtaccagca aaagagcggc     120
accagcccca agaggtggat ctacgacacc agcaagctgg ccagcggagt gcccgctaga    180
tttagcggca gcggcagcgg caccagctac tctttaacca tcagcagcat ggagaccgag    240
gacgtggcca cctactactg ccagcagtgg aacagcaacc ccccaccttt cggcactggt    300
accaagctgg agatcaag                                                  318
```

<210> SEQ ID NO 30
<211> LENGTH: 321
<212> TYPE: DNA
<213> ORGANISM: Artificial Sequence
<220> FEATURE:
<223> OTHER INFORMATION: DNA sequence of the constant region of the
      hu1F11 light chain

<400> SEQUENCE: 30

```
cgtacggtgg ccgcccccag cgtgttcatc tttccccca gcgacgagca gctgaagagc      60
ggcacagcca gcgtggtgtg cctgctgaac aacttctacc caggggaggc caaggtgcag    120
tggaaggtgg acaacgccct gcagagcggc aacagccagg agagcgtgac cgagcaggac    180
agcaaggaca gcacctacag cctgagcagc accctgaccc tgagcaaggc cgactacgag    240
aagcacaagg tgtacgcctg cgaggtgacc caccagggac tgagcagccc cgtgaccaag    300
agcttcaaca ggggcgagtg c                                              321
```

<210> SEQ ID NO 31
<211> LENGTH: 363
<212> TYPE: DNA
<213> ORGANISM: Artificial Sequence
<220> FEATURE:
<223> OTHER INFORMATION: DNA sequence of the variable region of the
      hu1F11 heavy chain

<400> SEQUENCE: 31

```
caagttcaac tgcagcagag cggcgccgaa ctggtgaaac cggtgccag cgtgaagctg       60 agctgcaaga cctccggctt caccttcagc agcagctaca tcagctgggt gaagcagagc    120
agcggccaag gtttagaatg gatcgcttgg atttacgccg gcaccggcgg cactggttat    180
aaccagaagt tcaccggtcg tgccagcatc accgtcgaca cctccaccag caccgcctac    240
atgcagctga gctctttaac cagcgaggac accgccatct actactgcgc catcagcgcc    300
agctatcgtt acgacgattt attcgcctac tggggacaag gtactttagt gaccgtgagc    360
agc                                                                  363
```

<210> SEQ ID NO 32
<211> LENGTH: 990
<212> TYPE: DNA
<213> ORGANISM: Artificial Sequence
<220> FEATURE:
<223> OTHER INFORMATION: DNA sequence of the constant region of the
      hu1F11 heavy chain

<400> SEQUENCE: 32

```
gctagcacca agggcccag cgtgtttcct ctggccccta gctccaagtc cacctccgga       60
ggaacagccg ccctgggatg cctcgtgaag gactacttcc ctgagcccgt gaccgtgtcc    120
tggaacagcg gagccctgac aagcggagtg cacaccttcc ccgccgtgct gcagtccagc    180
ggactgtaca gcctgagcag cgtggtgacc gtgccttcct ccagcctcgg cacccagacc    240
tacatctgca acgtgaacca caagccctcc aacacaaagg tcgacaagaa ggtggagccc    300
aagagctgcg acaagaccca cacctgccct cctgccctg ctcctgaact cctgggaggc    360
cccagcgtct tcctgtttcc ccccaaaccc aaggacacac tgatgatcag cagaaccct    420 gaggtgacct gcgtggtggt cgatgtgtcc cacgaggacc ccgaggtgaa gttcaattgg    480
tacgtggacg gcgtcgaggt gcacaacgcc aaaacaaagc ccagagaaga gcagtacgcc    540
tccacctaca gagtcgtgtc cgtgctgaca gtgctgcacc aggactggct gaacggcaag    600
```

```
gagtacaagt gcaaggtgag caacaaggcc ctgcctgccc ccatcgagaa gaccatcagc        660
aaggccaaag gccagcccag agagcctcag gtgtacaccc tgcccccccag cagggaagag       720 atgaccaaga atcaggtgag cctgacctgc ctggtgaaag gcttctatcc cagcgacatc       780
gccgtggagt gggagagcaa cggccagccc gagaacaact acaagaccac ccctcccgtg       840
ctggacagcg atggctcctt cttcctgtac agcaagctga ccgtggacaa gagcaggtgg       900
cagcagggca acgtcttcag ctgcagcgtg atgcatgagg ccctgcacaa ccattacacc       960
cagaagtccc tgagcctgtc ccctggcaag                                        990
```

<210> SEQ ID NO 33
<211> LENGTH: 10
<212> TYPE: PRT
<213> ORGANISM: Artificial Sequence
<220> FEATURE:
<223> OTHER INFORMATION: CDR-L1 of the variable region of the hu1F11
     light chain

<400> SEQUENCE: 33

Ser Ala Ser Ser Ser Val Ser Ser Val His
1               5                   10

US 12,325,749 B2

ANTI-PD-L1 ANTIBODY AND USE THEREOF

This is a United States national stage entry under 35 U.S.C. § 371 of International Application No. PCT/CN2019/096786, filed Jul. 19, 2019, the contents of which is incorporated herein by reference.

TECHNICAL FIELD

This disclosure relates generally to the therapy of cancer. In particular, this disclosure is related to a new anti-PD-L1 antibody and its medical use.

The instant application contains a Sequence Listing that has been submitted electronically in ST.25 format and is hereby incorporated by reference in its entirety. Said ST.25 copy, created on Mar. 14, 2025, is named 70262209_Substitute_Sequence_Listing.txt, and is 28.2 KB in size.

BACKGROUND

Programmed death-1 (PD-1) is a 288 amino acid protein receptor expressed on activated T-cells and B-cells, natural killer cells and monocytes. The primary function of PD-1 is to attenuate the immune response. PD-1 has two ligands, PD-ligand1 (PD-L1) and PD-L2. PD-L1 (CD274, B7H1) is expressed widely on both lymphoid and non-lymphoid tissues such as CD4 and CD8 T-cells, macrophage lineage cells, peripheral tissues as well as on tumor cells, virally-infected cells and autoimmune tissue cells. PD-L2 (CD273, B7-DC) has a more restricted expression than PD-L1, being expressed on activated dendritic cells and macrophages (Dong et al 1999, Nature Med.). PD-L1 is expressed in most human cancers, including melanoma, glioma, non-small cell lung cancer, squamous cell carcinoma of head and neck, leukemia, pancreatic cancer, renal cell carcinoma, and hepatocellular carcinoma, and may be inducible in nearly all cancer types (Zou and Chen 2008, Nat. Rev. Immunol. 8:467-77). PD-1 binding to its ligands results in decreased T-cell proliferation and cytokine secretion, compromising humoral and cellular immune responses in diseases such as cancer, viral infection and autoimmune disease. Blockade of PD-1 binding to reverse immunosuppression has been studied in autoimmune, viral and tumor immunotherapy (Ribas 2012, NEJM 366:2517-2519; Watanabe et al 2012, Clin. Dev. Immunol. Volume 2012, Article ID: 269756; Wang et al 2013, J. Viral Hep. 20:27-39).

SUMMARY

In one aspect of the present invention, an isolated antibody or antigen-binding fragment thereof that binds specifically to human PD-L1 protein is provided, wherein the antibody or antigen-binding fragment thereof comprises CDR-H1 as shown in SEQ ID NO:15, CDR-H2 as shown in SEQ ID NO: 17 and CDR-H3 as shown in SEQ ID NO: 19), and CDR-L1 as shown in SEQ ID NO:5, CDR-L2 as shown in SEQ ID NO:7 and CDR-L3 as shown in SEQ ID NO:9.

In some embodiments, the antibody or antigen-binding fragment thereof comprises a heavy chain variable region (HCVR) comprising the amino acid sequence of SEQ ID NO: 12, and a light chain variable region (LCVR) comprising the amino acid sequence of SEQ ID NO: 2.

In some embodiments, the antibody or antigen-binding fragment thereof is humanized, and comprises a heavy chain variable region (HCVR) comprising the amino acid sequence of SEQ ID NO:27, and a light chain variable region (LCVR) comprising the amino acid sequence of SEQ ID NO: 25.

In some embodiments, the antibody or antigen-binding fragment thereof comprises a heavy chain comprising the amino acid sequence of SEQ ID NO: 22, and a light chain comprising the amino acid sequence of SEQ ID NO: 21.

In some embodiments, the antibody or antigen-binding fragment thereof is in the form of Fab, Fab', F(ab')$_2$, scFv or bispecific antibody.

In another aspect of the present invention, a nucleic acid molecule encoding the isolated antibody or antigen-binding fragment thereof of the present invention is provided.

In some embodiments, the nucleic acid molecule comprises a nucleotide sequence selected from the group consisting of SEQ ID NO: 1, 11, 23, 24, 29 and 31.

Another aspect of the present invention provides a vector comprising the nucleic acid molecule of the present invention.

Another aspect of the present invention provides a host cell comprising the vector of the present invention.

In another aspect of the present invention, a pharmaceutical composition comprising the isolated antibody or antigen-binding fragment thereof according to any one of claims 1-5, and a pharmaceutically acceptable carrier is provided.

In some embodiments, the pharmaceutical composition further comprises a chemotherapeutic agent.

In some embodiments, the pharmaceutical composition is to be administered in combination with a radiotherapy.

In another aspect of the present invention, a method of treating a PD-L1 related disease in a subject is provided, the method comprising administering to the subject an therapeutically effective amount of the isolated antibody or antigen-binding fragment thereof of the present invention or an therapeutically effective amount of the pharmaceutical composition of the present invention.

In some embodiments, the PD-L1 related disease is a tumor which is PD-L1 positive.

In some embodiments, the tumor is selected from the group consisting of lymphoma, liver cancer, stomach cancer, lung cancer, colon cancer, pancreas cancer, and breast cancer.

In some embodiments, the isolated antibody or antigen-binding fragment thereof or the pharmaceutical composition is administered in combination with a chemotherapeutic agent and/or radiotherapy.

Another aspect of the present invention provides use of the isolated antibody or antigen-binding fragment thereof of the present invention in the preparation of a medicament for treating a PD-L1 related disease in a subject.

In some embodiments, the PD-L1 related disease is a tumor which is PD-L1 positive.

In some embodiments, the tumor is selected from the group consisting of lymphoma, liver cancer, stomach cancer, lung cancer, colon cancer, pancreas cancer, and breast cancer.

BRIEF DESCRIPTION OF THE FIGURES

FIGS. 1A-1D show the DNA and protein sequences of the variable regions in m1F11. FIG. 1A shows the DNA sequence of the variable regions in the light chain. FIG. 1B shows the protein sequence of the variable regions in the light chain. Residues and positions of light chain CDR1-3 and light chain frameworks are listed. FIG. 1C shows the DNA sequence of the variable regions in the heavy chain. FIG. 1D shows the protein sequence of the variable regions in the heavy chain. Residues and positions of heavy chain CDR1-3 and heavy chain frameworks are as listed.

FIGS. 6A-6L show sequences of humanized 1F11 (hu1F11). FIG. 6A shows the protein sequence of the hu1F11 light chain; FIG. 6B shows the protein sequence of the hu1F11 heavy chain; FIG. 6C shows the DNA sequence of the hu1F11 light chain; FIG. 6D shows the DNA sequence of the hu1F11 heavy chain; FIG. 6E shows the protein sequence of the variable region of the hu1F11 light chain; FIG. 6F shows the protein sequence of the constant region of the hu1F11 light chain; FIG. 6G shows the protein sequence of the variable region of the hu1F11 heavy chain; FIG. 6H shows the protein sequence of the constant region of the hu1F11 heavy chain; FIG. 6I shows the DNA sequence of the variable region of the hu1F11 light chain; FIG. 6I shows the DNA sequence of the constant region of the hu1F11 light chain; FIG. 6K shows the DNA sequence of the variable region of the hu1F11 heavy chain; FIG. 6L shows the DNA sequence of the constant region of the hu1F11 heavy chain.

FIG. 10 shows that hu1F11 maintains species selectivity measured by ELISA.
  A. Binding curve of hu1F11 (open triangles) and Atezolizumab (dots) with soluble monkey PD-L1.
  B. the binding $EC_{50}$ s ng/ml to monkey PD-L1 and $R^2$ of curve fitting.
  C. The binding curve of hu1F11 (open triangles) and Atezolizumab (dots) with soluble mouse PD-L1.
  D. The calculated $EC_{50}$ s ng/ml and $R^2$ of curve fitting.

DETAILED DESCRIPTION

Figure 2:
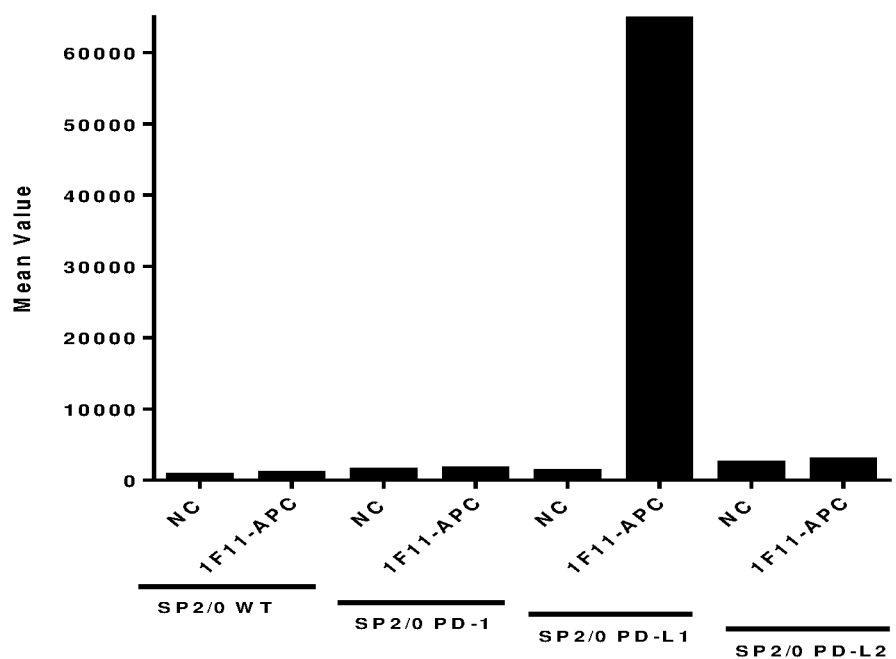
FIG. 2 shows that m1F11 specifically recognizes human PD-L1, but not PD-1 or PD-L2. SP2/0, SP2/0 PD-1, SP2/0 PD-L1, and SP2/0 PD-L2 cells were analyzed with flow cytometry after incubation with APC-labeled m1F11 or equal amount of buffer as negative control (NC). The y-axis shows the mean fluorescence value generated by binding between 1F11-APC and indicated cells listed on x-axis. Only SP2/0 PD-L1 cells generate a significant mean value over 60,000, while the rest have just a trace amount of signal.

It is to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

The term "PD-1" refers to the programmed death-1 protein, a T-cell co-inhibitor, also known as CD279. The amino acid sequence of full-length PD-1 is provided in GenBank as accession number NP_005009.2. The term "PD-1" includes recombinant PD-1 or a fragment thereof. The term also encompasses PD-1 or a fragment thereof coupled to, for example, histidine tag, mouse or human Fc, or a signal sequence such as ROR1.

The term "PD-L1" refers to the ligand of the PD-1 receptor also known as CD274 and B7H1. The amino acid sequence of full-length PD-L1 is provided in GenBank as accession number NP_054862.1. The term also encompasses PD-L1 or a fragment thereof coupled to, for example, histidine tag, mouse or human Fc, or a signal sequence such as ROR1. PD-L1 is a 290 amino acid protein with an extracellular IgV-like domain, a transmembrane domain and a highly conserved intracellular domain of approximately 30 amino acids. PD-L1 is constitutively expressed on many cells such as antigen presenting cells (e.g., dendritic cells, macrophages, and B-cells) and on hematopoietic and non-hematopoietic cells (e.g., vascular endothelial cells, pancreatic islets, and sites of immune privilege). PD-L1 is also expressed on a wide variety of tumors, virally-infected cells and autoimmune tissue, and is a component of the immunosuppressive milieu (Ribas 2012, NEJM 366:2517-2519).

The term "antibody", as used herein, includes but is not limited to, polyclonal antibody, monoclonal antibody, monospecific antibody, multispecific antibody (e.g., bispecific antibodies), single-chain antibody, humanized antibody, recombinant antibody and synthetic antibody. refers to an immunoglobulin or a fragment or a derivative thereof, and encompasses any polypeptide comprising an antigen-binding site. The term includes whole antibody (immunoglobulin) or any antigen-binding fragment (i.e. antigen-binding portion) or single chain thereof. The term "antibody" also includes antibody fragments, such as Fab, Fab', F(ab')$_2$, scFv or other antibody fragments that retain antigen-binding function, i.e., the ability to specifically bind PD-L1. Typically, such fragments would comprise an antigen-binding domain.

Antibody or immunoglobulin comprised of heavy (H) chain and light (L) chain, or antigen-binding fragments thereof. Each heavy chain is comprised of a heavy chain variable region ("HCVR" or "VH") and a heavy chain constant region (CH, comprised of domains CH1, CH2 and CH3). Each light chain is comprised of a light chain variable region ("LCVR or "VL") and a light chain constant region (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The terms "CDR", and its plural "CDRs", refer to a complementarity determining region (CDR) of which three make up the binding character of a light chain variable region (CDR-L1, CDR-L2 and CDR-L3) and three make up the binding character of a heavy chain variable region (CDR-H1, CDR-H2 and CDR-H3). CDRs contribute to the functional activity of an antibody molecule and are separated by amino acid sequences that comprise framework regions. The exact definitional CDR boundaries and lengths are subject to different classification and numbering systems. CDRs may therefore be referred to by Kabat and/or Chlothia.

The anti-PD-L1 antibody of the present invention comprises SASSSVSSMH (SEQ ID NO: 5) or SASSSVSSVH (SEQ ID NO:33), DTSKLAS (SEQ ID NO:7), and QQWNSNPPT (SEQ ID NO:9) as CDR-L1, CDR-L2 and CDR-L3 respectively, and comprises SSYIS (SEQ ID NO:15), WIYAGTGGTGYNQKFTG (SEQ ID NO:17), and SASYRYDDLFAY (SEQ ID NO:19) as CDR-H1, CDR-H2 and CDR-H3 respectively.

As used herein, the term "antigen-binding portion" of an antibody (or simply "antibody portion") or "antigen-binding fragment" of an antibody (or simply "antibody fragment"), refers to one or more fragments of an antibody that retain the ability to specifically bind to an antigen, e.g., PD-LI, preferably the antigen binding and/or the variable region of the intact antibody. Examples of binding fragments encompassed within the term "antigen-binding portion" or "antigen-binding fragment" include Fab, Fab', F(ab')$_2$ and Fv fragment; single-chain antibody and multispecific antibody (e.g. bispecific antibody). Fab fragment is a monovalent fragment consisting of the VH, VL, CL and CHI domains. Fab fragment consists of an entire light chain along with the variable region domain of the heavy chain (VH), and the first constant domain of one heavy chain (CH1). Each Fab fragment is monovalent with respect to antigen binding, i.e., it has a single antigen-binding site. F (ab') 2 fragment is a bivalent fragment comprising two Fab fragments linked by a disulfide bridge at the hinge region. Fv fragment consists of the VH and VL domains of a single arm of an antibody. Furthermore, although the two domains of the Fv fragment, VH and VL, are coded for by separate genes, they can be joined, using recombinant methods, by a synthetic linker that enables them to be made as a single protein chain in which the VH and VL regions pair to form monovalent molecules (known as single chain Fv (scFv); see e.g., Bird et al (1988) Science 242:423 426; and Huston et al (1988) Proc. Natl. Acad. Sci. USA 85:5879 5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "multispecific antibody", as used herein, refers to bispecific or multispecific antibody and antigen-binding fragments thereof. The multispecific antibody may be specific to different epitopes of a target polypeptide or may contain specific antigen binding domains for epitopes of more than one target polypeptide. A multispecific antibody can be a single multifunctional polypeptide, or it can be a multimeric complex of two or more polypeptides that are associated with each other covalently or non-covalently. The term "multispecific antibody" includes antibodies of the present invention that may be linked or co-expressed with another functional molecule, e.g., another peptide or protein. For example, an antibody or fragment thereof can be functionally linked (e.g., by chemical coupling, genetic fusion, non-covalent association or otherwise) to one or more molecular entities, such as a protein or fragment thereof to produce a bispecific molecule or a multispecific molecule of antigen binding with a second binding specificity. According to the present invention, the expression "multispecific antibody" also includes bispecific, trispecific or multispecific antibodies or antigen binding fragments thereof. In certain embodiments, an antibody of the present invention is functionally linked to another antibody or antigen-binding fragment thereof to produce a bispecific antibody with a second binding specificity. In some embodiments, multispecific antibodies may refer to a multispecific one that bind to a PD-L1 domain and one or more additional antigens or a bispecific one that binds to two different regions of PD-L1.

As used herein, the term "isolated" antibody is intended to refer to an antibody which is substantially free of other antibodies having different antigenic specificities (e.g., an isolated antibody that specifically binds to PD-LI is substantially free of antibodies that do not bind to PD-L1). In addition, an isolated antibody is typically substantially free of other cellular material and/or chemicals. Purification of antibodies is well known to those skilled in the art.

The term "monoclonal antibody" as used herein refers to an antibody obtained from a substantially homogeneous population, i.e., the individual antibodies comprised in the population are identical except for occasionally possible naturally occurring mutations and/or post-translation modifications. Monoclonal antibodies are highly specific, being directed against a single antigenic determinants (epitopes). Monoclonal antibodies may be produced by a variety of techniques, including, for example, the hybridoma method or the recombinant DNA methods and the like, which are well known to those skilled in the art. The antibody of the present invention may be a chimeric antibody or a humanized antibody.

The term "chimeric antibody" refer to an antibody in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity. In some embodiments, the term "chimeric antibody" is intended to refer to antibodies in which the variable region sequences are derived from one species and the constant region sequences are derived from another species, such as an antibody in which the variable region sequences are derived from a non-human antibody (e.g. a murine antibody) and the constant region sequences are derived from a human antibody. The constant region sequence may be derived from those of human IgG, such as IgG1, IgG2, IgG3 or IgG4 or variants thereof, or from those of human kappa class or lambda class. The constant region of the chimeric antibody may be mutated to reduce undesired effect, such as antibody-dependent cellular cytotoxicity (ADCC) and complement-dependent cytotoxicity (CDC) effect. As used herein, "humanized antibody" is used a subset of "chimeric antibodies."

As used herein, the term "humanized antibody" refers to an antibody that consists of CDR derived from a non-human (such as murine) antibody, and FR region and the constant region of a human antibody. A humanized antibody is useful as an effective component in a therapeutic agent according to the present invention since antigenicity of the humanized antibody in human body is lowered. In general, at least one and preferably all of CDRs of a humanized antibody are derived from a non-human (such as murine) antibody, and all or substantially all of the FR regions are derived from a human antibody, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3.

Antibodies of the invention may be generated or produced by any technique known in the art, such as, without limitation, any chemical, biological, genetic or enzymatic technique, either alone or in combination. Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, California) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In particular embodiments, the invention relates to a nucleic acid sequence encoding the VH domain or the VL domain of the antibody of the invention. The nucleic acid may encode the heavy chain or the light chain of the antibody of the invention. Typically, said nucleic acid is a DNA or RNA molecule, which may be included in any suitable vector, such as a plasmid, cosmid, episome, artificial chromosome, phage or a viral vector. In general, nucleic acid constructs include a regulatory sequence, such as a promoter, enhancer, terminator and the like, operably linked to the encoding nucleotide sequence. Regulatory sequences (also referred to as expression control sequences) typically do not encode a gene product, but instead affect the expression of the nucleic acid sequences to which they are operably linked.

The terms "vector" mean the vehicle by which a DNA or RNA sequence (e.g. encoding the anti-PD-L1 antibody of the present invention) can be introduced into a host cell, so as to transform the host and expression of the introduced sequence. So, a further object of the invention relates to a vector comprising the nucleic acid of the invention. Such vectors may directly express the antibody upon administration to a subject. Alternatively, an expression vector may be used to be introduced into a host cell to produce the antibody in vitro.

A further object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein coded by the introduced gene or sequence. A host cell that receives and expresses introduced DNA or RNA has been "transformed". The nucleic acids of the invention may be used to produce an antibody of the invention in a suitable expression system. Examples of host cells include, but is not limited to, prokaryotic cells, such as bacterial cells (e.g. *E. coli*); or eukaryotic cells, such as yeast, mammalian cells, insect cells, plant cells, etc. Examples of mammalian host cells include, but is not limited to human embryonic kidney 293 cells, CHO cells, etc.

Anti-PD L1 antibodies can be isolated using, for example, chromatographic methods such as DEAE ion exchange, gel filtration, and hydroxylapatite chromatography. For example, anti-PD LI antibodies in a cell culture supernatant or a cytoplasmic extract can be isolated using a protein G or protein A column.

The present invention also provides a composition, e.g., a pharmaceutical composition, containing one or a combination of antibodies, or antigen-binding portion(s) thereof, of the present invention, formulated together with a pharmaceutically acceptable carrier. The term "pharmaceutical composition" refers to a preparation that is in such form as to permit the biological activity of the active ingredient to be effective, and that contains no additional components that are unacceptably toxic to a subject to which the formulation would be administered. The pharmaceutical compositions of the invention may comprise other therapeutic agents, and also may be administered in combination therapy, i.e., combined with other therapeutic agents or therapy.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, e.g., antibody, may be coated in a material to protect the antibody from the action of acids and other natural conditions that may inactivate the antibody. In particular aspects, the invention provides a method of treating a PD-L1 related disease in a subject, comprising administering to the subject an effective amount of the antibody or the pharmaceutical composition of the invention.

A PD-L1 related disease may a disease characterized by the expression of PD-L1 on the cell surface or a disease which can be treated by inhibiting PD-LI function by using a PD-LI antagonist (e.g. anti-PD-L1 antibody). A disease characterized by the expression of PD-L1 on the cell surface may also be called a PD-LI positive disease. Those skilled in the art have known many PD-LI related diseases, such as PD-LI positive disease, including cancer, tumor, autoimmune disease and inflammatory disease, etc.

Cancers or tumors that can be treated by the antibodies or the pharmaceutical composition of the invention include cancers or tumors typically responsive to immunotherapy. Non-limiting examples include lymphoma, melanoma (e.g., metastatic malignant melanoma), renal cancer, prostate cancer, breast cancer, colon cancer, liver cancer, stomach cancer, pancreas cancer and lung cancer. Examples of other cancers that may be treated using the methods of the invention include bone cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers and tumors. The present invention is also useful for treatment of metastatic cancers, especially metastatic cancers that express PD-L1.

The term "treat", "treating" or "treatment" refers to clinical intervention designed to alter the natural course of the subject being treated, and can be performed either for prophylaxis or during the course of clinical pathology. Desirable effects of treatment include preventing occurrence or recurrence of disease, preventing metastasis, decreasing the rate of disease progression, ameliorating or palliating the disease state, and remission or improved prognosis. In some embodiments, antibodies of the invention are used to delay development of a disease or disorder. A subject is successfully "treated", for example, using the anti-PD-L1 antibodies of the invention if one or more symptoms associated with PD-L1 positive disease is mitigated.

As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount that produces the desired effect for which it is administered, such as a decrease in severity of disease symptoms, an increase in frequency and duration of disease symptom-free periods, or a prevention of impairment or disability due to the disease affliction. A therapeutically effective amount herein may vary according to factors such as the disease state, age, sex, and weight of the patient, and the ability of the antibody to elicit a desired response in the individual. For example, a therapeutically effective amount of the anti-PD-L1 antibodies of the present invention is at least the minimum concentration that results in inhibition of at least one symptom of a PD-LI positive disease. For example, for the treatment of PD-LI positive tumors, a "therapeutically effective amount" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. One of ordinary skill in the art would be able to determine such amounts based on such factors as the subject's size, the severity of the subject's symptoms, and the particular composition or route of administration selected.

The antibody or the pharmaceutical composition of the present invention can be administered via one or more routes of administration using one or more of a variety of methods known in the art. As will be appreciated by the skilled artisan, the route and/or mode of administration will vary depending upon the desired results. Preferred routes of administration for the antibodies or the pharmaceutical composition of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the antibody or the pharmaceutical composition of the invention can be administered via a non-parenteral route, such as a topical, epidermal or mucosal route of administration, for example, intranasally, orally, vaginally, rectally, sublingually or topically.

Determination of the appropriate dose may be made using parameters or factors known or suspected in the art to affect treatment or predicted to affect treatment. The antibodies or the pharmaceutical composition can be provided by continuous infusion, or by doses at intervals of, e.g., one day, one week, or 1-7 times per week. A preferred dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 25 mg/kg, or at least 50 mg/kg.

The pharmaceutical compositions of the invention may comprise other therapeutic agents. The antibody or the pharmaceutical composition of the invention may be administered in combination therapy, i.e., combined with other therapeutic agents or therapy, such as surgery, chemotherapy and radiation. Said other therapeutic agents may include cytotoxic, cytostatic, anti-angiogenic or antimetabolite agent, a tumor targeted agent, an immune stimulating or immune modulating agent, such as a chemotherapeutic agent. The antibody or the pharmaceutical composition of the invention may be administered simultaneously or sequentially with other therapeutic agents.

A "chemotherapeutic agent" is a chemical compound useful in the treatment of cancer. Examples of chemotherapeutic agents include alkylating agents such as thiotepa and cyclophosphamide; alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and butlatacinone); delta-9-tetrahydrocannabinol (dronabinol); beta-lapachone; lapachol; colchicines; betulinic acid; a camptothecin (including the synthetic analogue topotecan (CPT-11 (irinotecan), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenestenne, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gammaII and calicheamicin omegaII (see, e.g., Nicolaou et ah, Angew. Chem Intl. Ed. Engl., 33:183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, doxorubicin HCl liposome injection and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine, tegafur, capecitabine, an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); thiotepa; taxoids, e.g., paclitaxel, albumin-engineered nanoparticle formulation of paclitaxel, and doxetaxel; chloranbucil; 6-thioguanine; mercaptopurine; methotrexate; platinum analogs such as cisplatin and carboplatin; vinblastine; platinum; etoposide (VP-16); ifosfamide; mitoxantrone; vincristine; oxaliplatin; leucovovin; vinorelbine; novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin combined with 5-FU and leucovovin.

Other therapeutic agents that may be used in combination with the anti-PD-L1 antibodies of the invention are bisphosphonates such as clodronate, NE-58095, zoledronic acid/zoledronate, alendronate, pamidronate, tiludronate, or risedronate; as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as Stimuvax vaccine, Theratope vaccine and gene therapy vaccines, for example, Allovectin vaccine, Leuvectin vaccine, and Vaxid vaccine; topoisomerase 1 inhibitor; an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; arinotecan; rmRH; lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

The term "about" as used herein refers to the usual error range for the respective value readily known to the skilled person in this technical field.

The fully human anti-PD-L1 monoclonal antibodies disclosed herein may comprise one or more amino acid substitutions, insertions and/or deletions in the framework and/or CDR regions of the heavy and light chain variable domains as compared to the corresponding germline sequences.

As used herein the singular forms "a", "an", and "the" include plural referents unless the context clearly dictates otherwise.

Example 1: A New Anti-PD-L1 Antibody 1F11 Effectively Reverses Immune Suppression Abstract: In the tumorigenesis, the program death-1 receptor/program death ligand-1 (PD-1/PD-L1) signaling pathway contributes to the immune evasion of host immune response. PD-L1, depending on its physiological and pathological distribution, could negatively regulate T cell activation, restrict T cell trafficking and compromise T cell cytotoxicity. Anti-PD-L1 antibody is clinically efficacious in cancer treatment by blocking PD-1/PD-L1 axis. In this paper, a novel anti-PD-L1 antibody, named 1F11, is identified in BALB/C mice immunized with Chinese hamster ovary (CHO) cells expressing human PD-L1. It specifically binds human and monkey PD-L1, but not the mouse counterpart. It demonstrates a comparable affinity to Atezolizumab and Avelumab in binding with either soluble or membrane PD-L1. A panel of 94 human tumor cells screening found that 1F11 has a broad spectrum of recognizing tumor PD-L1 expression at varying levels. 1F11 competes the binding of PD-L1 with PD-1, and results in reversing immunosuppression caused by PD-1/PD-L1. In the INFγ releasing experiment with human and monkey peripheral blood mononuclear cells (PBMCs), 1F11 boosts the production of INFγ, suggesting that it enhances the function of immune cells. The profile of 1F11, consisted of a strong affinity, broad recognizing spectrum and reasonable biological activity, delineates a novel therapeutic anti-PD-L1 antibody for cancer treatment.

Introduction: Immune checkpoints consist of receptors and ligands functioning as co-stimulators and co-inhibitors that tune the T cell-based immune response. Off-balance of either plays a significant role in ailments, for example autoimmune diseases due to overactive (Ceeraz et al 2014) or cancers for insufficient immune response (Dong et al 2002). Blockage of cytotoxic T lymphocyte-associated antigen (CTLA-4) and/or the program death-1 receptor/program death ligand-1 (PD-1/PD-L1), especially the later, has brought great clinical benefits in multiple cancers (Sun et al 2018). Though only a small proportion of patients respond to immune checkpoint treatment, the longtail survival outcome of the respondents really casts some light on the hope of curing cancer. As such, a huge resource has been spent on developing new immune checkpoint therapies.

The PD-1/PD-L1 signaling pathway remains in the spotlight, albeit a number of assets have been approved in the market. Initially, it is considered that the tumor cell PD-L1 inhibiting T cell cytotoxicity is sufficient for immune evasion (Juneja et al 2017). Later, it is discovered that the host cell PD-L1 is critical for suppressing anti-tumor immunity (Tang and Zheng 2018, Lau et al 2017). This finding is consistent with the clinical benefit observed in patients whose tumors were PD-LI negative. The efficacy may result from reversing the PD-L1 from inhibiting T cell trafficking and activation by PD-1/PD-L1 blockage in host tissues (Tang et al 2018). Therefore, a comprehensive evaluation of PD-L1 expression in organs beyond tumors may offer better criteria in predicting the responsive population in PD-1/PD-L1 blockage. Meanwhile, it also suggests that more patients may be benefited from the PD-1/PD-L1 blockage treatment.

In this article, we introduce a novel anti-PD-L1 antibody 1F11. It specifically recognizes human and monkey PD-L1 with a high affinity comparable to Atezolizumab and Avelumab, the approved drugs on the market. It also elicits a decent biological activity in reversing immunosuppression.

Materials and Methods:

Materials: The following reagents were purchased from Southern Biotech and used in indicated dilution: goat anti-mouse IgG-HRP (1030-05,1:5000 dilution), Goat anti-human IgG-PE (2040-09,1:1000 dilution), Goat anti-Human Kappa IgG-HRP (2061-05, 1:20000 dilution), Streptavidin-FITC (7100-02, 1:500 dilution), Mouse anti-human Kappa-APC (9230-11,1:500 dilution), Mouse IgG-APC (0107-11, 0.1 mg/ml), Goat anti-mouse IgG-HRP (1030-05, 1:20000 dilution). huPD-1-hFc-Biotin (10377-H03H-B), Mouse PD-L1-his (50010-M08H), Cynomolgus PD-L1-his (90251-C08H), and CD3e-FITC (10977-H08H, 0.1 mg/ml,1:100 dilution) were products of Sino Biological, Human PD-L1-hFc (B3040) was purchased from Biointron Biological Inc. IFNY (AFL285) was from R&D system. 1F11-APC (1 mg/ml, 1:1000 dilution) and EU-anti-IFN-γ 3B5 (1:5000 dilution) were prepared in house. Atzeolizumab and Avelumab were prepared in house or purchased from commercial resource. In house generated Atzeolizumab was validated with commercial antibody (Tecentriq) in binding affinity. Cell culture medium Roswell Park Memorial Institute (RPMI) 1640, Dulbecco's modified eagle's medium (DMEM) and fetal bovine serum were from Hyclone.

Cell culture: Cell lines used in the research were purchased from and maintained in the appropriate medium recommended by ATCC. SP2/0 PD-1, SP2/0 PD-L1, SP2/0 PD-L2 stably expressing human PD-1, human PD-L1 and human PD-L2 respectively, and Chinese hamster ovary (CHO) cells expressing human PD-LI were generated in house.

Enzyme-linked immunosorbent assay (ELISA): ELISA was run according to the reference (Hornbeck et al) with baits and detecting secondary antibodies detailed in the text.

Fluorescence activated cell sorting (FACS)/flow cytometry: FACS was performed as detailed in the reference (Holmes et al 2001), with slight modification.

Generation of anti-PD-L1 hybridoma: On day one, BALB/c mice (female, age of 8-10 weeks), were intraperitoneally injected with 1-2×10$^6$ CHO cells expressing human PD-L1 together with Freund's complete adjuvant. On day 8, an enhanced immunization was performed with the same amount of cells with Freund's incomplete adjuvant. Since day 14, every three days mice were immunized with the abovementioned amount of cells, and repeated three times. Three days after the last immunization, B lymphocytes from spleens were isolated and fused with immortal myeloma cells NS-1 cells to generate hybridoma cells.

The hybridoma cells were cultured in a 96-well plate, in a series dilution. The supernatants were collected to screen any antibody that recognizes PD-L1 expressed on the surface of SP2/0 cells by flow cytometry.

DNA cloning and sequencing of antibody variable regions: Briefly, total RNA extracted from the hybridomas with Trizol (ThermoFisher) was reversely transcribed into the first cDNA strands. Rapid amplification of 5' complementary DNA (5'RACE) followed by nested PCR was then adapted to amplify the DNA sequence encoding the variable regions, as described in the instruction of 5'RACE kit (Invitrogen, 18374-058). The PCR products were cloned into pGM-T vector. Positive clones were proceeded for DNA sequencing, from which the protein sequences were deduced accordingly. The amino acids of the variable regions were analyzed in Kabat numbering scheme.

Humanization: First, murine-human chimeric antibody was generated by replacing the constant regions of the murine antibody with sequence of human IgG1 constant regions. Meanwhile, to reducing the antibody-dependent cellular cytotoxicity (ADCC) and complement-dependent cytotoxicity (CDC) effect, Asparagine at site 297 (N297) in the heavy chain was mutated to Alanine (A).

Humanization was then processed on top of chimeric antibody, following the procedure in the reference (Kuramochi et al). The residues in the mouse framework essential for maintaining the affinity and specificity were preserved while replacing mouse framework with human germline framework to generate humanized antibody.

The DNA sequences of optimized codons encoding the chimeric and humanized antibodies were synthesized in GenScript.

Antibody expression: In short, DNA encoding the antibody heavy chain and light chain were cloned into the expression vector pCDNA3.1 (+) (Invitrogen) and expressed in the 293T cells. Antibodies were purified with protein A or G columns (GE).

Surface plasmon resonance (SPR): kinetics and affinity were determined with Biacore T200. Briefly, recombinant human PD-L1-Fc was immobilized on the CM5 chip. Antibodies at concentrations from 12.5 nM to a final 0.025 nM, generated by a 2-fold serial dilution, were run through the chip to determine the affinity and kinetics.

INFγ releasing from human and monkey peripheral blood mononuclear cells (PBMCs): PBMCs were isolated from the human blood donated by healthy volunteer, or monkey blood purchased from Beijing Sharing Institute of Resources. In a U-bottom 96-well plate, each well was added 25 ul of PBMCs at $2\times10^6$ cells/ml, staphylococcal enterotoxin B (SEB) to a final working concentration of 100 ng/ml or equal volume of culture medium as control, and antibody to final working concentrations as indicated. After 72 hr incubation at 37° C., 5% $CO_2$, the supernatants were collected to determine INFγ.

Results:

Hybridoma Generation and the Antibody Sequence Cloning

Anti-human PD-L1 antibody was generated by immunizing BALB/c mice with CHO cells that expressing human PD-L1 on the surface. Hybridoma was developed by fusing mouse spleen B lymphocyte with myeloma cell NS-1. Supernatant from culture hybridoma was detected by ELISA (data not shown) to identify the clones producing anti-PD-L1 antibodies. 1F11 was one of the positive clones chosen for further characterization. The murine antibody derived from this clone was thereafter called m1F11.

Total RNA was then extracted from the 1F11 hybridoma and subjected to 5'RACE and nested PCR. Following cloning into the pGM-T vector, the amplified PCR products were proceeded to DNA sequencing. The nucleic acid sequences of the light chain and heavy chain are shown in FIG. 1A,C. The encoding protein sequences are presented in FIGS. 1B and D. The amino acid sequences were analyzed with Kabat numbering scheme. CDR residues and positions were identified and listed in FIGS. 1B and D. Comparing with sequences in the public domain found that 1F11 is a novel anti-PD-L1 antibody.

Generation and Characteristics of Anti-PD-L1 Murine Antibody m1F11

The recombinant m1F11 was then expressed in CHO—S cells and purified for further characterization.

For anti-PD-L1 antibody to elicit any function in vivo, it is critical that the antibody should recognize PD-L1 resembling its physiological and pathological presence. Therefore, the m1F11 capacity of recognizing membrane anchored PD-LI was initially confirmed by flow cytometry as shown in FIG. 2. Briefly, APC-labeled m1F11 was incubated with SP2/0 cells expressing different human sourced proteins. The association between m1F11 and cells were indicated by the mean fluorescence value detected by flow cytometry. The higher the value, the stronger the binding is. In this experiment, m1F11 bound with SP2/0 PD-L1 cells and generated a value over 60,000, but just a trace signal with SP2/0 wild type (wt), SP2/0 PD-1, or SP2/0 PD-L2. Together, it reveals that m1F11 specifically recognizes PD-L1, but not PD-1, PD-L2 or any other surface protein on SP2/0 cells.

Figure 3:
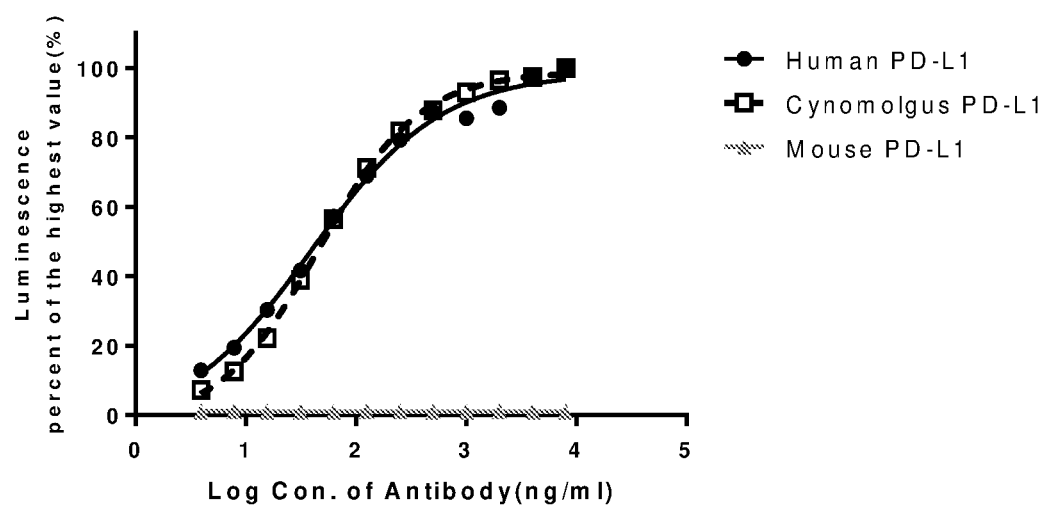
FIG. 3 shows that m1F11 selectively recognizes human and monkey PD-L1, but not murine PD-L1. (A). The plot is the binding curve of m1F11 with human, monkey PD-L1, and murine PD-L1. The Y-axis shows the relative luminescence index after incubation with various concentrations of antibody. The X-axis shows the logarithm of the antibody concentrations (ng/ml). (B). The $EC_{50}$ s(ng/ml) calculated from the plot in A and the $R^2$ of every curve are listed in the table.

The species selectivity of m1F11 was measured by ELISA. In short, a binding curve was generated by incubating recombinant human, cynomolgus and mouse PD-L1 s with various concentrations of the APC-labeled m1F11. As shown in FIG. 3A, there are full binding curves with both human and monkey PD-L1, but it remains flat with mouse PD-L1, indicating no binding between m1F11 and mouse PD-L1. Calculated from the plot, $EC_{50}$S of m1F11 binding with human and monkey PD-L1 s are 39.26 ng/ml and 46.42 ng/ml respectively (FIG. 3B).

Figure 4:
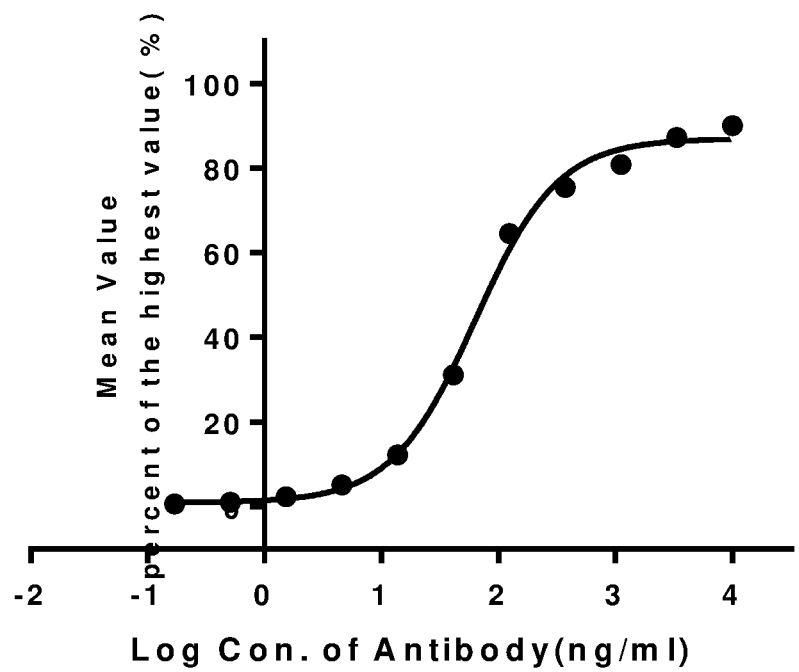
FIG. 4 shows the binding affinity between m1F11 and SP2/0 PD-L1. (A). Affinity between m1F11 and cell surface human PD-L1 was measured by incubating 1F11-APC with SP2/0 PD-L1 followed by flow cytometry. The Y-axis of the plot shows the relative fluorescence index after incubating with various concentration of 1F11, while the x-axis is the logarithm of the 1F11 concentrations (ng/ml). (B). The $EC_{50}$ (ng/ml) calculated from the plot in A and the $R^2$ of the curve are showed in the table.

The m1F11 binding affinity with membrane huPD-L1 (human PD-L1) was assessed by incubating various concentrations of APC-labeled m1F11 with SP2/0 PD-L1. A full binding curve was developed as showed in FIG. 4. $EC_{50}$ of m1F11 binding with cell surface PD-L1 is 62.89 ng/ml, at the similar range to its affinity with soluble PD-L1.

Figure 5:
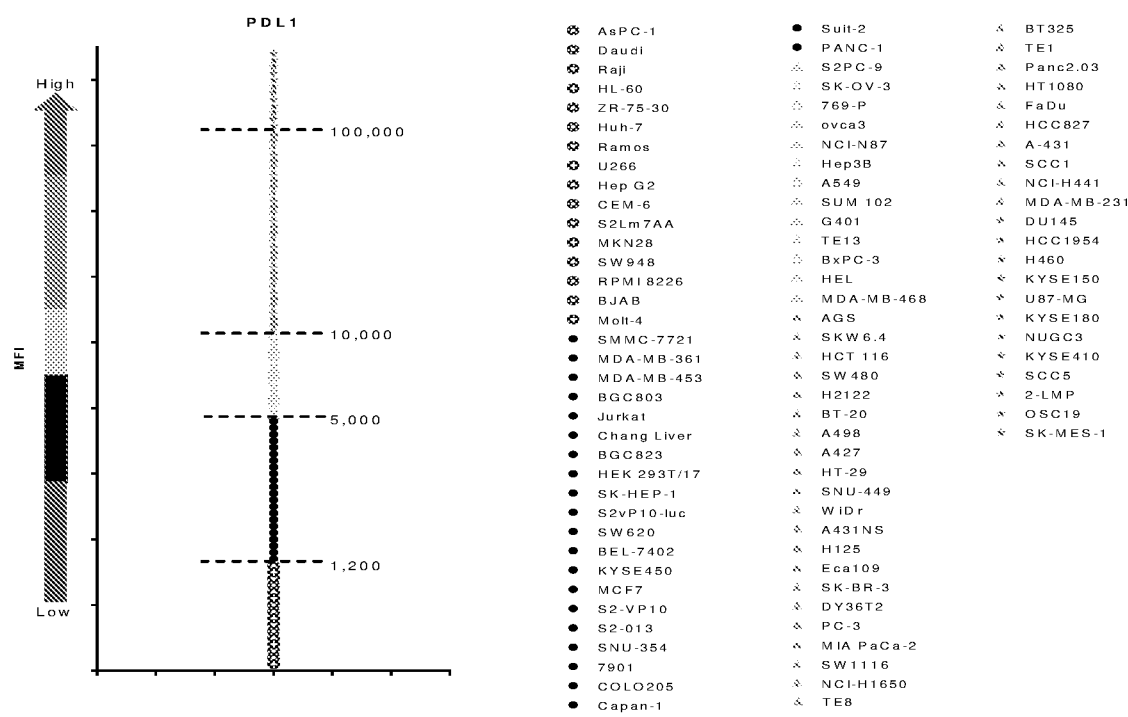
FIG. 5 shows clusters of tumor cell lines by their binding profile with m1F11. A total of 94 human tumor cell lines were profiled by flow cytometry to determine their surface level of PD-L1. Cells were incubated with 1F11-APC, and the surface level of PD-L1 was measured by the mean fluorescence index. Cells with an index above 100,000 are clustered in the group of the highest amount of surface PD-L1 (red solid stars). Those with a mean index between 100,000 and 10,000 are clustered in the second group (brown solid triangles). Cells with a value between 10,000 and 5,000 are in the third tier (green open triangles) those between 5000 and 1200 are in the fourth group as PD-L1 positive cells (black dots), while those cells with a value blow 1200 are considered PD-L1 negative (blue circles).

Moreover, the binding property between m1F11 (murine PD-L1) and cell surface PD-L1 was evaluated broadly with a panel of 94 human tumor cell lines derived from lymphoma and solid tumors of liver, stomach, lung, colon, pancreas, breast et al. The abundance of cell surface PD-LI was revealed by the fluorescence value of the associated APC-labeled m1F11. Results in FIG. 5 show that tumor cells express variable amount of PD-L1. An arbitrary cutoff at 1200 differentiates PD-L1 positive cells from negative ones. Cells with a mean APC fluorescence value less than 1200 are considered PD-L1 negative (marked in blue circle). The PD-LI positive cells are also arbitrarily clustered into four groups based on the mean values. Those cells with a value over 100,000 are in the group of expressing the highest amount cell surface PD-L1 (marked in red stars), followed by second highest group with a mean value between 100,000 and 10,000 (marked in brown filled triangles), the third group with a value between 10,000 and 5,000 (marked in green open triangles), and the fourth group with minimal level of PD-L1 of a value falling between 5000 and 1200 (marked in black dots). This finding of cell surface abundance of PD-L1 is consistent with reports in the literature (Rom-Jure et al, Kluger et al). This data shows that m1F11 recognized a broad spectrum of cell surface PD-L1 on multiple tumor cells.

In general, m1F11 demonstrates species selectivity against human and monkey PD-L1 and it recognizes cell surface huPD-L1 with $EC_{50}$ at the two digits ng/ml. Moreover, it binds tumor cell PD-L1 at a broad spectrum. As such, m1F11 could be a therapeutic tool in dealing with a variety of cancers.

Characterization of Humanized IF11 (hu1F11)

1F11 was humanized, as described in the material and method section. The nucleic and amino acid sequences of humanized 1F11 (hu1F11) were listed in FIG. 6. The murine human chimeric 1F11 (ch1F11) was generated by replacing the mouse constant region in the m1F11 with human IgG1 constant region. There are N297A mutations in the heavy chains to reduce the ADCC and CDC effect of the Fc region, in both ch1F11 (chimeric 1F11) and hu1F11. Antibodies were expressed in the 293T cells and purified with protein A columns. Binding affinity and species selectivity of hu1F11 were characterized in a number of assays, including SPR, ELISA, and FACS. In some cases, it was head-to-head compared with the US Food and Drug Administration (FDA) approved Atezolizumab (trade name: Tecentriq; CAS number: 1380723-44-3) and Avelumab (trade name: Bavencio; CAS number: 1537032-82-8).

Figure 7:
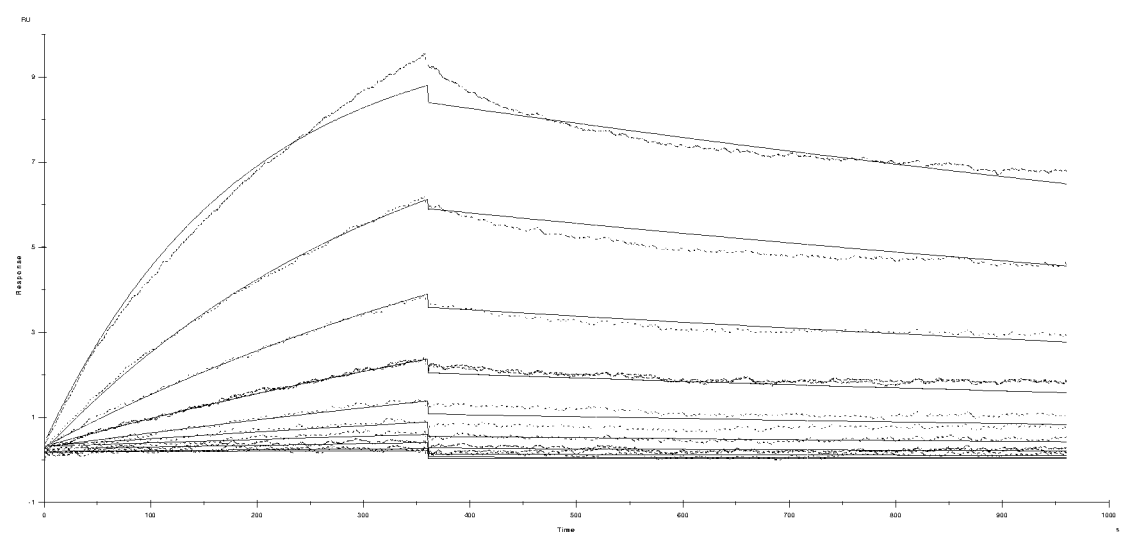
FIG. 7 shows affinity and kinetics of hu1F11 and PD-L1 interaction. (A) The sensogram reflects the binding response in resonance units (Y-axis) over time (x-axis, in seconds). The analyte concentrations from top curve down are 12.5 nM to 0.025 nM in a 2-fold series dilution. (B) The tables show the association rate constant ka, dissociation rate constant kd, affinity $K_D$, maximal binding capacity Rmax, $Chi^2$ reflecting the goodness of curve fitting, and the antibody-antigen binding mode.

First, hu1F11 binding affinity with human PD-LI was determined by SPR at Biacore T200. The hu1F11 at 10 concentrations from 12.5 down to 0.025 nM in a 2-fold dilution run through CM5 chip coated with hu-PD-L1-Fc. The sensorgram is showed in FIG. 7A. The y-axis is the resonance unit, while the x-axis is the observed duration with 300 seconds on association phase and 600 seconds on dissociation phase. As listed in FIG. 7B, the association rate constant ($k_a$) and dissociation rate constant ($k_d$) of hu1F11 binding with huPD-L1 are $2.09\times10^5$/Ms, and $5.76\times10^{-4}$/s, respectively. The dissociation constant $K_D$ is $2.75\times10^{-9}$ M, calculated by the equation: $K_D=kd/ka$. The association and dissociation rates match the property of the antibody-antigen binding.

Figure 8:
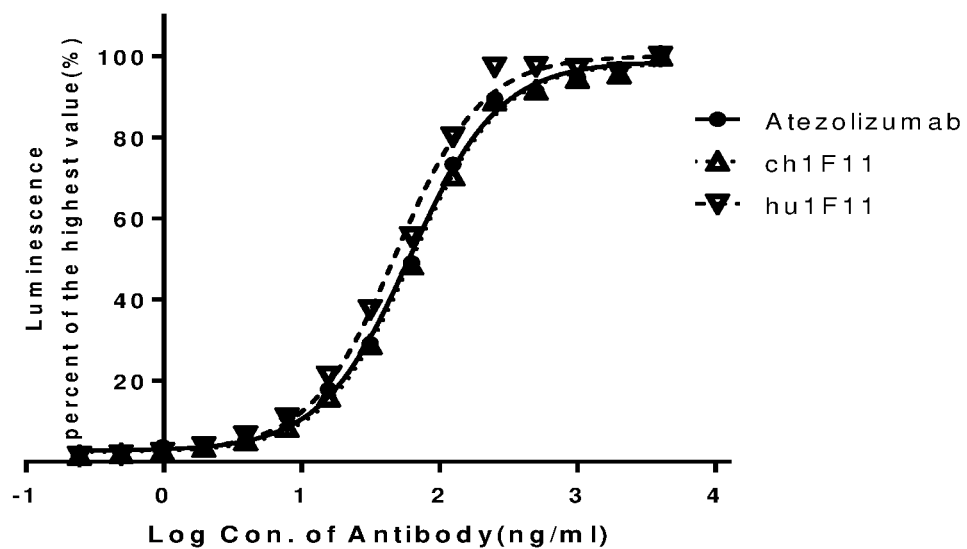
FIG. 8 shows the binding curve of hu1F11 with human PD-L1. A. The Y-axis shows the relative luminescence index generated after incubation with various concentrations of antibodies. The X-axis shows the logarithm of the antibody concentrations (ng/ml). B. The $EC_{50}$ s(ng/ml) of Atezolizumab, ch1F11 and hu1F11 calculated from the plot in A and the $R^2$ of every curve are showed in the table.

The affinity of hu1F11 binding with PD-L1 is comparable to that of Atzeolizumab or/and Avelumab, measured by ELISA and flow cytometry. The binding curves of the antibodies with soluble huPD-L1 are showed in FIG. 8A, the y-aixs is the relative luminescence index generated by antibody/antigen binding, while x-axis is the logarithm of antibody concentrations (ng/ml). hu1F11 was tested in parallel with Atezoliumab and ch1F11. As seen, binding curve of hu1F11 is slightly left-shifted compared with ch1F11 and Atezolizumab. $EC_{50}$ s calculated from the curves echo the binding curves, as hu1F11 has an $EC_{50}$ at 48.28 ng/ml, similarly potent to Atezolizumab and ch1F11, whose $EC_{50}$ s are 61.13 ng/ml and 63.36 ng/ml, respectively (FIG. 8B).

Figure 9:
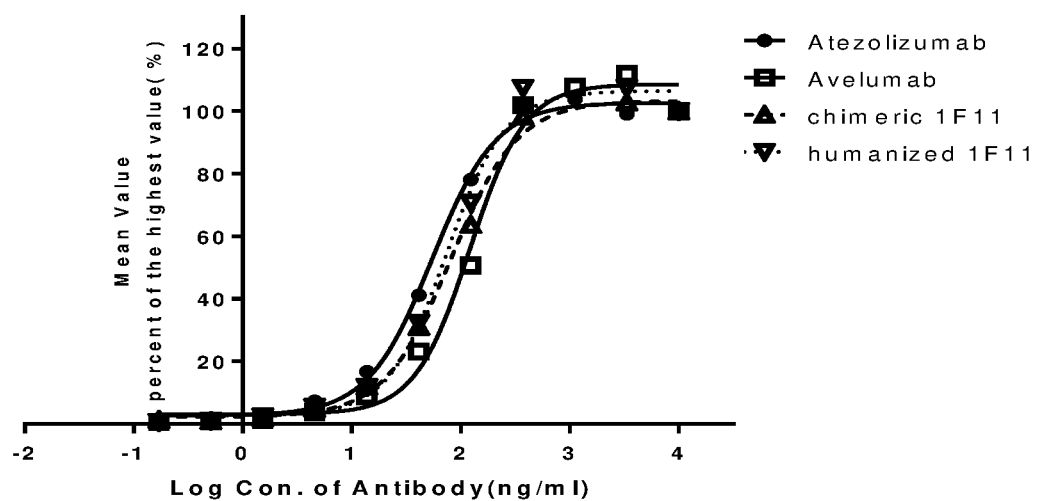
FIG. 9 shows binding affinity between hu1F11 and cell surface PD-L1. A. The plot is the binding curve of humanized 1F11 with SP2/0 PD-1. Chimeric 1F11, and two control antibodies Atezolizumab and Avelumab were tested in parallel as well. SP2/0 PD-L1 cells were analyzed with flow cytometry after incubation with APC-labeled antibodies. The y-axis shows the relative mean fluorescence value generated by binding between 1F11-APC. X-axis shows the logarithm of the tested antibody concentrations (ng/ml). B. The $EC_{50}$ s(ng/ml) of Atezolizumab, Avelumab, ch1F11 and hu1F11, calculated from the plot in A and $R^2$ of the curves.

The binding curves with cell surface PD-L1 (FIG. 9A) further reveal that the affinities of hu1F11, ch1F11 and Atezolizumab are in the same range, with $EC_{50}$ s at 74.24, 81.01 and 54.45 ng/ml, respectively, while Avelumab is less potent with an $EC_{50}$ at 120.9 ng/ml, as seen in FIG. 9B.

hu1F11 maintains the species selectivity confirmed in m1F11. Binding affinity of hu1F11 and Atezolizumab with monkey and mouse PD-LI were measured by ELISA. Binding curves are showed in FIGS. 10A and 10C. Y-axis is the relative luminescence index generated by antibody/antigen binding and x-axis is the logarithm of antibody concentrations (ng/ml). Atzeolizumab recognizes mouse PD-L1 with an $EC_{50}$ of 18.88 ng/ml (FIG. 10D), while hu1F11, similar to m1F11, could not recognize mouse PD-L1 (FIG. 10C). hu1F11 and Atzeolizumab are almost identically potent at binding with monkey PD-L1, with $EC_{50}$ s at 15.26 and 12.36 ng/ml respectively (FIG. 10B).

Overall, hu1F11 maintains the species selectivity of recognizing human and monkey PD-L1. Its binding affinities with human and monkey PD-L1 are close to those of Atezolizumab and Avelumab.

Biological Activity of hu1F11 hu1F11 biological activities were assessed in PD-L1/PD-1 blockage, competitively displacing the huPD-1 from SP2/0 PD-L1 and function in promoting INFγ releasing from PBMCs.

Figure 11:
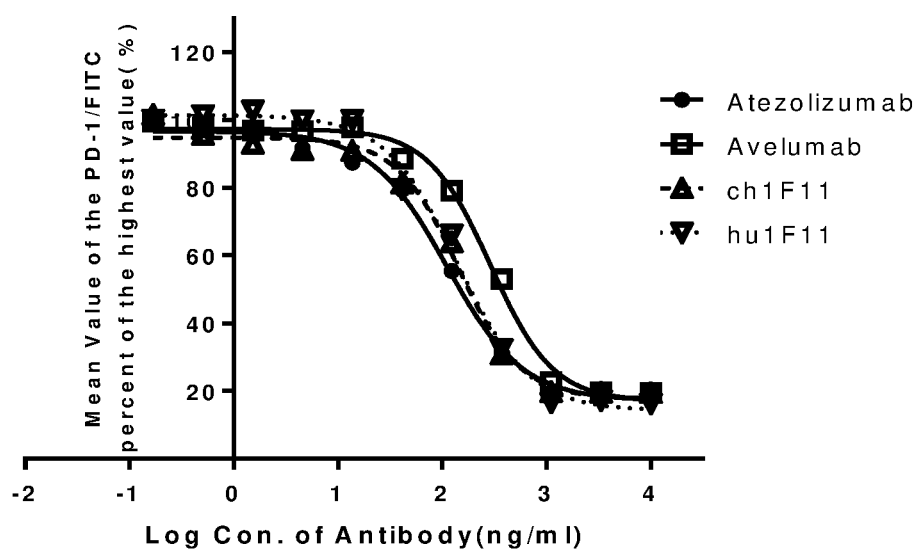
FIG. 11 shows that hu1F11 blocks the interaction between huPD-1 and SP2/0 PD-L1. A. The efficacy of hu1F11 in blocking the interaction between soluble PD-1 and cell surface PD-L1 was determined by flow cytometry, in parallel with ch1F11, Atezolizumab and Avelumab. Y-axis is the relative fluorescence value resulted from the interaction between antibodies and SP2/0 PD-L1. X-axis shows the logarithm of the antibody concentrations (ng/ml). B. $IC_{50}$ s of Atezolizumab, Avelumab, ch1F11 and hu1F11 in huPD-1/PD-L1 blockage, and the $R^2$ of the fitting curves.

FIG. 11 shows the hu1F11 efficacy in blocking the interaction between biotin-labeled huPD-1 and SP2/0 PD-L1 cells. The y-axis shows that relative fluorescence value generated from biotin-huPD-1/SP2/0 PD-L1 complex detected by streptavidin-FITC, and the x-axis are the working concentrations of the tested antibodies. As the concentrations of the antibodies increase, the fluorescence value of the huPD-1/SP2/0 PD-L1 decrease, suggesting that antibodies block the PD-1/SP2/0 PD-L1 interaction. The $IC_{50}$ s of hu1F11 in the PD-1/SP2/0 PD-LI blockage is 139.6 ng/ml, and those of ch1F11, Atezolizumab and Avelumab are 143.2, 110 and 289.7 ng/ml respectively (FIG. 11B).

Figure 12:
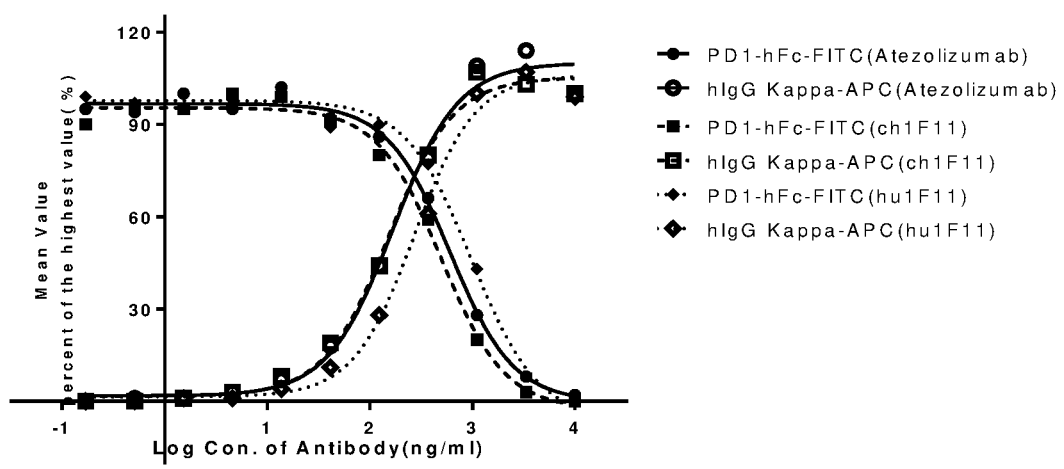
FIG. 12 shows that hu1F11 displaces huPD-1 from the huPD-1/SP2/0 PD-L1 complex. SP2/0 PD-L1 cells were incubated with biotin-labeled huPD-1 recombinant protein. Antibodies at various concentrations were then applied to compete with the membrane associated huPD-1. The y-axis shows the relative fluorescence index of the remaining huPD-1 and the competitive antibodies that displaced it, which were measured by FITC-streptavidin and APC-labeled anti-human IgG, respectively. X-axis shows the logarithm of antibody concentrations (ng/ml). The reversed S-shape curves demonstrate that the membrane associated huPD-1 decreases as the concentrations of antibodies increase, meanwhile the membrane associated competitive antibodies gradually increase as indicated by relative APC signal on the s-shape curves.

A second assay was run similarly as in FIG. 11, but an APC-labeled anti-human IgG was added to detect the competitive antibodies that block PD-1/SP2/0 PD-L1. As seen in FIG. 12, while the signal of PD-1/PD-L1 decreases showed by the reverse S-shape curves, that of the antibody/PD-LI increases as it is in the S-shape curves. The trend is the same for hu1F11 and Atezolizumab. Taking together, data in FIGS. 11 and 12 illustrate that hu1F11compete the PD-1/PD-L1 binding, in a mode similar to Atzeolizumab.

Figure 13:
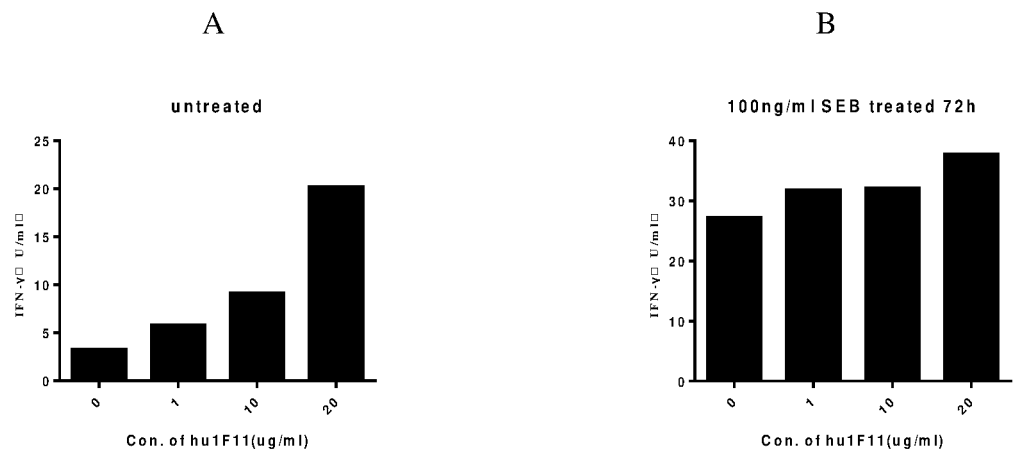
FIG. 13 shows the effects of hu1F11 on INFγ production by human PBMCs. Human PBMCs were either untreated (A) or activated by SEB (B) for 72 hours at the presence of various concentrations of hu1F11. The INFγ released into the culture medium were measured by ELISA.
Figure 14:
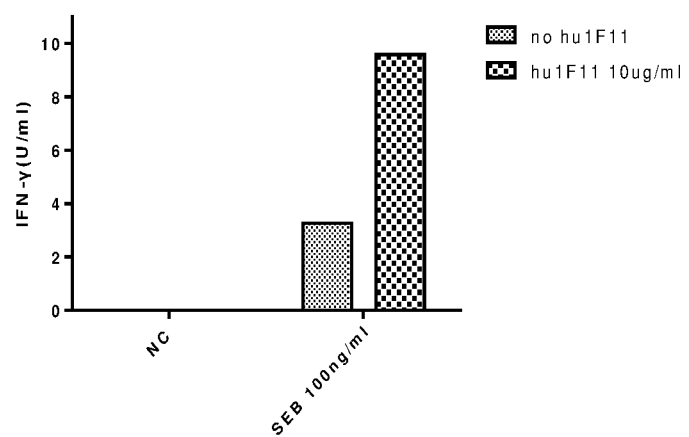
FIG. 14 shows the effects of hu1F11 on INFγ production by monkey PBMCs. Monkey PBMCs were either untreated (NC) or activated by SEB for 72 hours at the presence of 10 ug/ml hu1F11. The INFγ released into the culture medium was measured by ELISA. The INFγ concentration is showed in the Y-axis. There is no baseline INFγ releasing at resting status. When activated by SEB, INFγ in the medium reaches 3.26 U/ml, and 9.59 ug/ml treatment pushes it up to 10 U/mL.

The biological activity of hu1F11 in antagonizing immunosuppression was evaluated by IFNγ releasing from the PBMCs. PBMCs from healthy volunteer and monkey were cultured with or without the presence of 100 ng/ml SEB and various amount of hu1F11. 72 h later, the culture medium was collected to measure the INFγ released by the PBMCs. SEB greatly upregulates the PD-L1 and PD-1 levels (Data not showed), suggesting an immunosuppression status. FIG. 13A shows the INFγ concentration in the culture medium released by the SEB-untreated human PBMCs. The INFγ concentration was 3 U/ml without hu1F11. With the presence of 1, 10, and 20 ug/ml hu1F11, it was increased by 100%, 200% and 567% to 6, 9 and 20 U/ml, respectively. FIG. 13B shows the result from SEB-activated human PBMCs. The presence of hu1F11 at 1, 10 and 20 ug/ml boosted the INFγ to 31, 32, and 38 U/ml, a 15%, 19% and 41% increase respectively from 27 U/ml without 1F11. In the experiment with monkey PBMCs, there was no baseline activation of the monkey PBMCs, as such no INFγ was detected in the untreated group. In contrast, after treated with SEB, INFγ was significantly upregulated. With the presence of 10 ug/ml hu1F11, INFγ was increased to 9.59 u/ml, around a 2-fold increase from 3.26 u/ml without hu1F11, as showed in FIG. 14. This data indicates that hu1F11 can reverse the immunosuppression in the PBMCs. The effects of hu1F11 in promoting IFNγ releasing from both human and monkey PBMCs are consistent with its species selectivity.

In summary, 1F11 is a novel antibody against PD-L1. It specifically binds human and monkey PD-L1, with a comparable affinity to Atezolizumab and Avelumab, two anti-PD-L1 antibodies approved for clinical therapy. It blocks the PD-L1/PD-1 interaction, and more importantly, the blocking effect reverses immunosuppression caused by PD-1-PD-L1 axis.

DISCUSSION

1F11 is a novel antibody anti-PD-L1. It was identified from the mice immunized with CHO cells expressing full human length PD-L1, by which to a largest extent mimics the physiological status and tertiary structure of the antigen. Profiling with a series of assays containing PD-L1 either in soluble format or on cell surface demonstrates that 1F11 broadly recognizes its antigen in both physiological and pathological contexts.

The murine version 1F11 was humanized by grafted the murine CDRs into the human germline framework and IgG1 constant regions, while a few key residues in the mouse framework are preserved to maintain its affinity. A mutation is contained in the Fc region (N297A) to reduce ADCC and CDC effects. The codons of hu1F11 were optimized and transient expression in CHO—S produced 100 mg/L purified active antibody (Data not shown), a reasonable start point to establish stable cell line resulting in sufficient yield.

hu1F11 preserves the species selectivity and affinity observed in its murine counterpart. Evaluation with a variety of assays reveals that its blocking effect and affinity are comparable to Atzeolizumab and Avelumab, two marketed drugs of its kind. Noteworthily, it demonstrates the unique feature of displacing PD-L1 out of the PD-1/PD-L1 complex, which neither of its competitors could fulfil. More work is required to investigate if this translates into better clinical benefit.

In summary, 1F11 is a novel anti-PD-L1 antibody with a unique feature. Its clinical advantage is yet to unfold.

REFERENCES

Ceeraz S, Nowak E C, Burns C M, Noelle R J. Immune checkpoint receptors in regulating immune reactivity in rheumatic disease. Arthritis Res Ther. 2014; 16 (5): 469.

Dong H, Strome S E, Salomao D R, Tamura H, Hirano F, Flies D B, Roche P C, Lu J, Zhu G, Tamada K, Lennon V A, Celis E, Chen L. Tumor-associated B7-H1 promotes T-cell apoptosis: a potential mechanism of immune vasion. Nat Med. 2002 August; 8 (8): 793-800.

Holmes, K., Lantz, L., Fowlkes, B J., Schmid, I. and Giorgi. J. Current Protocols in Immunology (2001) 5.3.1-5.3.24

Hornbeck, P., Winston, S. E., & Fuller, S. A. (2001). Enzyme-Linked Immunosorbent Assays (ELISA). Current Protocols in Molecular Biology.

Juneja V R, McGuire K A, Manguso R T, LaFleur M W, Collins N, Haining W N, Freeman G J, Sharpe A H. PD-L1 on tumor cells is sufficient for immune evasion in immunogenic tumors and inhibits CD8 T cell cytotoxicity. J Exp Med. 2017 Apr. 3; 214 (4): 895-904.

Kuramochi T, Igawa T, Tsunoda H, Hattori K. Humanization and simultaneous optimization of monoclonal antibody. Methods Mol Biol. 2014; 1060:123-37.

Kluger H M, Zito C R, Turcu G, Baine M K, Zhang H, Adeniran A, Sznol M, Rimm D L, Kluger Y, Chen L, Cohen J V, Jilaveanu L B. PD-1 Studies Across Tumor Types, Its Differential Expression and Predictive Value in PatientsTreated with Immune Checkpo int Inhibitors. Clin Cancer Res. 2017 Aug. 1;23 (15): 4270-4279.

Lau J, Cheung J, Navarro A, Lianoglou S, Haley B, Totpal K, Sanders L, Koeppen H, Caplazi P, McBride J, Chiu H, Hong R, Grogan J, Javinal V, Yauch R, Irving B, Belvin M, Mellman I, Kim J M, Schmidt M. Tumour and host cell PD-L1 is required to mediate suppression of anti-tumour immunity in mice. Nat Commun. 2017 Feb. 21; 8:14572.

Rom-Jurek E M, Kirchhammer N, Ugocsai P, Ortmann O, Wege A K, Brockhoff G. Regulation of Programmed Death Ligand 1 (P D-L1) Expression in Breast Cancer Cell Lines In Vitro and in Immunodeficient and Humanized Tumor Mice. Int J Mol Sci. 2018 Feb. 13;19 (2). pii: E563.

Sun C, Mezzadra R, Schumacher T N. Regulation and Function of the P D-L1 Checkpoint. Immunity. 2018 Mar. 20;48 (3): 434-452.

Tang F, Zheng P. Tumor cells versus host immune cells: whose P D-L1 contributes to PD-1/PD-L1 blockade mediated cancer immunotherapy? Cell Biosci. 2018 May 2; 8:34.

Tang H, Liang Y, Anders R A, Taube J M, Qiu X, Mulgaonkar A, Liu X, Harrington S M, Guo J, Xin Y, Xiong Y, Nham K, Silvers W, Hao G, Sun X, Chen M, Hannan R, Qiao J, Dong H, Peng H, Fu Y X. PD-L1 on host cells is essential for PD-L1 blockade-mediated tumor regression. J Clin Invest. 2018 Feb. 1: 128 (2): 580-588.

The invention claimed is:

1. An isolated antibody or antigen-binding fragment thereof that binds specifically to human PD-L1 protein, wherein the antibody or antigen-binding fragment thereof comprises CDR-H1 as shown in SEQ ID NO:15, CDR-H2 as shown in SEQ ID NO: 17, and CDR-H3 as shown in SEQ ID NO:19, and CDR-L1 as shown in SEQ ID NO:5 or SEQ ID NO: 33, CDR-L2 as shown in SEQ ID NO:7, and CDR-L3 as shown in SEQ ID NO:9.

2. The isolated antibody or antigen-binding fragment thereof of claim 1, wherein the antibody or antigen-binding fragment thereof comprises a heavy chain variable region (HCVR) comprising the amino acid sequence of SEQ ID NO: 12, and a light chain variable region (LCVR) comprising the amino acid sequence of SEQ ID NO: 2.

3. The isolated antibody or antigen-binding fragment thereof of claim 1, wherein the antibody or antigen-binding fragment thereof comprises a heavy chain variable region (HCVR) comprising the amino acid sequence of SEQ ID NO:27, and a light chain variable region (LCVR) comprising the amino acid sequence of SEQ ID NO:25.

4. The isolated antibody or antigen-binding fragment thereof of claim 3, wherein the antibody or antigen-binding fragment thereof comprises a heavy chain comprising the amino acid sequence of SEQ ID NO: 22, and a light chain comprising the amino acid sequence of SEQ ID NO: 21.

5. The isolated antibody or antigen-binding fragment thereof of claim 1, wherein the antibody or antigen-binding fragment thereof is in the form of Fab, Fab', F(ab')$_2$, scFv or bispecific antibody.

6. A nucleic acid molecule encoding an isolated antibody or antigen-binding fragment thereof of claim 1.

7. The nucleic acid molecule of claim 6, which comprises a nucleotide sequence selected from the group consisting of SEQ ID NO: 1, 11, 23, 24, 29, and 31.

8. A vector comprising a nucleic acid molecule of claim 6.

9. A host cell comprising the vector of claim 8.

10. A pharmaceutical composition comprising the isolated antibody or antigen-binding fragment thereof according to claim 1, and a pharmaceutically acceptable carrier.

11. The pharmaceutical composition of claim 10, further comprising a chemotherapeutic agent.

12. The pharmaceutical composition of claim 10, which is to be administered in combination with a radiotherapy.

13. A method of treating a PD-L1 positive tumor in a subject in need thereof, comprising administering to the subject a therapeutically effective amount of the isolated antibody or antigen-binding fragment thereof according to claim 1.

14. The method of claim 13, wherein the tumor is selected from the group consisting of lymphoma, liver cancer, stomach cancer, lung cancer, colon cancer, pancreas cancer, and breast cancer.

15. The method of claim 13, wherein the isolated antibody or antigen-binding fragment thereof is administered in combination with a chemotherapeutic agent and/or radiotherapy.

16. The isolated antibody or antigen-binding fragment thereof of claim 1, wherein the antibody or antigen-binding fragment thereof is humanized.

* * * * *